United States Patent [19]

Alexander et al.

[11] Patent Number: 6,103,103

[45] Date of Patent: Aug. 15, 2000

[54] DEHYDROGENATION CATALYST AND PROCESS

[75] Inventors: Bruce D. Alexander; George A. Huff, Jr., both of DuPage; Mark P. Kaminsky, Winfield, all of Ill.

[73] Assignee: BP Amoco Corporation, Chicago, Ill.

[21] Appl. No.: 09/250,643

[22] Filed: Feb. 16, 1999

Related U.S. Application Data

[63] Continuation of application No. 08/270,435, Jul. 5, 1994, abandoned.

[51] Int. Cl.⁷ .......................... C07C 5/333; C07C 5/327; C10G 35/04
[52] U.S. Cl. .......................... 208/134; 208/133; 208/138; 585/660; 585/654
[58] Field of Search ..................................... 208/133, 134, 208/138; 585/660, 654

[56] References Cited

U.S. PATENT DOCUMENTS

| | | | |
|---|---|---|---|
| 4,269,813 | 5/1981 | Klotz | 423/277 |
| 4,433,190 | 2/1984 | Sikkenga et al. | 585/660 |

*Primary Examiner*—Walter M. Griffin
*Assistant Examiner*—Tam M. Nguyen
*Attorney, Agent, or Firm*—Robert A. Yesukevich

[57] ABSTRACT

A process and catalyst are provided for dehydrogenating a hydrocarbon feedstock and producing an olefinic product. The process comprises contacting the feedstock at dehydrogenation conditions with a dehydrogenation catalyst comprising from about 0.01 weight percent to about 5.0 weight percent of a platinum group metal, from about 0.02 weight percent to about 10.0 weight percent of zinc, and a support component comprising borosilicate and an alkali metal.

10 Claims, No Drawings

DEHYDROGENATION CATALYST AND PROCESS

This is a continuation of application Ser. No. 08/270,435 filed Jul. 5, 1994, now abandoned.

BACKGROUND OF THE INVENTION

This invention relates to a process and catalyst for the dehydrogenation of hydrocarbons. More particularly, this invention relates to a catalyst and process for the dehydrogenation of paraffinic hydrocarbon utilizing a catalyst comprising a platinum group metal and zinc on a support component comprising borosilicate and an alkali metal, useful for the production of high oxygen-content fuels blending components (Oxygenates) and chemical industry feedstocks.

Oxygenates have been part of the United States gasoline strategy since the late 1970s. With the recent enactment of the Clean Air Act Amendments of 1990, the demand for oxygenates has increased again such that gasoline is now being blended to 2.7 weight percent oxygen and is being marketed in numerous metropolitan areas that have failed to meet carbon monoxide pollution standards. In the near future, it is expected that between 30 and 60 percent of the United States gasoline pool may require oxygenates.

The most commonly used oxygenates today are methanol, ethanol, and ethers such as methyl tertiary butyl ether (MTBE). Although methanol and ethanol have high blending octanes, problems with toxicity, water miscibility, high Reid Vapor Pressure (RVP), high nitrogen oxide emissions, lower fuel efficiency, and cost have dampened industry enthusiasm for these components. As a result of the above, MTBE has become particularly attractive.

Homologues of MTBE such as ethyl tertiary butyl ether (ETBE) and methyl tertiary amyl ether (TAME) are also gaining industry acceptance. Moreover, commercial activity with respect to ETBE and TAME is expected to increase relative to MTBE, in view of recent Environmental Protection Agency decisions to reduce the RVP requirements for gasolines well below 9 psia, the blending RVP of MTBE.

Ether production capacity, however, is often limited by iso-olefin feedstock availability. Commercial MTBE and ETBE processes both utilize isobutylene as a feedstock while TAME processes utilize isoamylene as a feedstock. Isobutylene and isoamylene are generally supplied to a commercial ether process from a fluid catalytic cracking unit (FCC), a fluidized or delayed coker, or from downstream paraffin isomerization and dehydrogenation facilities. As a result, the availability of hydrocarbons having 4 or 5 carbon atoms is limited by constraints such as, but not limited to, crude properties, FCC catalyst properties and operating conditions, coking conditions, as well as by other refinery operating constraints. The chemical mix of $C_4$ and $C_5$ paraffins, olefins, and aromatics as well as the particular mix of iso-olefins to normal olefins are similarly constrained.

The relatively high ratio of capital and operating costs to the throughput of ether product subsequently produced from the construction of new facilities for increasing ether process feedstocks further exacerbates oxygenate supply. These costs are generally attributed to the high degree of complexity and the sophisticated equipment connected to the operation of dehydrogenation or isomerization processes such as, but not limited to, desulfurization, catalytic reactor, and hydrogen supply and recirculation systems. The profitability of such new facilities is often dependent on the ability of the refiner to keep construction costs low and operating throughput high.

Thus, there exists a great need in the petroleum industry for a low cost method of increasing oxygenate production feedstocks that overcomes or avoids the obstacles described above and that is economically viable in terms of construction cost and facility utilization.

Processes for dehydrogenating paraffins in the presence of hydrogen and a catalyst comprising a platinum group metal on an amorphous alumina support have been disclosed in the art.

For example, U.S. Pat. Nos. 4,190,521, 4,374,046, and 4,458,098 to Antos disclose a catalyst comprising a platinum group component, nickel, and a zinc on a porous carrier material such as alumina for dehydrogenating paraffinic hydrocarbon.

U.S. Pat. No. 4,438,288 to Imai et al. discloses a dehydrogenation process using a catalyst comprising a platinum group component, an alkali or alkaline earth component, and optionally a Group IV component such as tin, on a porous support material such as alumina. The properties and characteristics of the catalyst generally necessitate periodic catalyst regeneration in the presence of a halogen.

Processes for dehydrogenating paraffins in the presence of hydrogen and a catalyst comprising a platinum group metal on an aluminosilicate or silicalite molecular sieve support have also been disclosed in the art.

For example, U.S. Pat. Nos. 4,665,267 and 4,795,732 to Barri and U.S. Pat. Nos. 5,208,201, and 5,126,502 to Barri et al. disclose processes for dehydrogenation of $C_2$ to $C_{10}$ paraffins using a catalyst comprising zinc and a platinum group metal on a support having the silicalite structure wherein the framework of the structure consists essentially of silicon and oxygen atoms or of silicon, zinc, and oxygen atoms. The catalyst is generally formed such that it is substantially free of all alkali or alkaline earth metals.

U.S. Pat. No. 4,727,216 to Miller discloses a process for dehydrogenating isobutane in the presence of a sulfur-containing gas and a dehydrogenation catalyst. The dehydrogenation catalyst comprises a sulfided L zeolite containing from 8–10% by weight barium, from 0.6–1.0% platinum, and tin at an atomic ratio with the platinum of about 1:1. The dehydrogenation catalyst further comprises an inorganic binder selected from the group consisting of silica, alumina, and aluminosilicates.

A process for dehydrogenating paraffins in the presence of hydrogen and a catalyst comprising a platinum group metal on a non-zeolitic borosilicate molecular sieve support has been disclosed in the art.

U.S. Pat. No. 4,433,190 to Sikkenga et al. discloses a process for dehydrogenating and isomerizing a substantially linear alkane using a dehydrogenation catalyst comprising an AMS-1B crystalline borosilicate-based catalyst composition and containing a noble metal.

While the above-described processes and catalysts have achieved varying degrees of laboratory success, it has been found that in commercial application, catalysts such as those described above have been prone to early deactivation and short on-stream run lengths. In order to overcome this obstacle, the process operator has generally needed to perform the dehydrogenation reaction in the presence of supplemental hydrogen for reducing catalyst coke formation. Supplemental hydrogen supply facilities are particularly complex and generally require costly compression and hydrogen purification equipment. Moreover, supplemental hydrogen addition drives the dehydrogenation reaction stoichiometrically away from dehydrogenation and towards olefin saturation.

Notwithstanding the presence of supplemental hydrogen addition and recirculation equipment, the process operator has still generally needed to resort to catalyst regeneration. Catalyst regeneration is generally performed in large, high temperature catalyst regenerators present in fluidized bed/riser schemes or through periodic and frequent batch regeneration such as performed with semi-regenerative fixed bed schemes. Catalyst regeneration facilities are extremely costly. For fixed bed reaction schemes, an additional swing reactor must be erected and the process operated with at least one reactor off-stream and in regeneration mode all of the time.

It has now been found that a dehydrogenation catalyst comprising a platinum group metal and zinc on a support comprising borosilicate and an alkali metal provides superior dehydrogenation performance in terms of paraffin conversion, olefin selectivity, and olefin yield to that of the prior art dehydrogenation catalysts and maintains such level of superior performance, without regeneration, far longer than any of the prior art catalysts tested to date.

It has also been found that a dehydrogenation catalyst comprising a platinum group metal and zinc on a support comprising borosilicate and an alkali metal provides such an extended operating cycle life, that it can be used with or without supplemental hydrogen addition while still achieving superior levels of performance.

For purposes of the present invention, paraffin conversion, olefin selectivity, and olefin yield shall have the following meanings and shall be calculated by mole and in accordance with the following models:

$$\text{Paraffin Conversion} = \frac{100 - \text{Mol \% H}_{2\,\text{product}} - \text{Mol \% Paraffin}_{\text{product}}}{100 - \text{Mol \% H}_{2\,\text{product}}} \times 100$$

$$\text{Olefin Selectivity} = \frac{\text{Mol \% Olefin}_{\text{product}}}{100 - \text{Mol \% H}_{2\,\text{product}} - \text{Mol \% Paraffin}_{\text{product}}} \times 100$$

$$\text{Olefin Yield} = \frac{(\text{Olefin Selectivity}) \times (\text{Paraffin Conversion})}{100}$$

It is therefore an object of the present invention to provide a dehydrogenation process and catalyst that effectively dehydrogenate paraffinic hydrocarbon.

It is another object of the present invention to provide a dehydrogenation catalyst that resists deactivation and prolongs catalyst cycle life under dehydrogenation conditions.

It is yet another object of the present invention to provide a dehydrogenation process and catalyst that can be effectively operated in the absence of supplemental hydrogen addition.

It is still another object of the present invention to provide a dehydrogenation process that, in view of its simplicity, can be adapted to utilize equipment from any of several existing petroleum refinery or chemical plant operating facilities.

Other objects appear herein.

SUMMARY OF THE INVENTION

The above objects can be achieved by providing a process for dehydrogenating a hydrocarbon feedstock and producing an olefinic product comprising contacting the feedstock at dehydrogenation conditions with a dehydrogenation catalyst comprising from about 0.01 weight percent to about 5.0 weight percent of a platinum group metal, from about 0.02 weight percent to about 10.0 weight percent of zinc, and a support component comprising borosilicate and an alkali metal.

In another embodiment, the above objects can be achieved by providing a dehydrogenation catalyst comprising from about 0.01 weight percent to about 5.0 weight percent of a platinum group metal, from about 0.02 weight percent to about 10.0 weight percent of zinc, a borosilicate molecular sieve, and from about 0.10 weight percent to about 10.0 weight percent of an alkali metal.

The dehydrogenation catalyst and process of the present invention provide superior overall dehydrogenation properties and particularly extraordinary levels of paraffin conversion closely approaching thermodynamic equilibrium. The paraffin conversion and olefin selectivity attendant to the dehydrogenation catalyst and process of the present invention generally result in olefin yield levels in excess of 25 percent, typically in excess of 35 percent, and commonly in excess of 40 percent.

The dehydrogenation catalyst and process of the present invention provide the above-described levels of performance while resisting deactivation under dehydrogenation conditions, thereby extending catalyst cycle life. The dehydrogenation catalyst of the present invention can and has achieved olefin yield deactivation loss levels of 0.6 percent conversion per day or less at a reaction temperature of $1050°$ F. and 1.1 percent conversion or less at reaction temperatures of $1075°$ F.

The dehydrogenation catalyst and process of the present invention can be utilized for on stream periods in excess of 400 hours at a reaction temperature of $1000°$ F. before requiring catalyst regeneration or replacement. The dehydrogenation catalyst and process of the present invention are so effective with regard to catalyst stability and deactivation resistance that the catalyst can be operated in the absence of supplemental hydrogen addition. Operating in the absence of supplemental hydrogen addition not only avoids enormous capital and operating costs connected to the installation and operation of hydrogen recovery facilities but also favorably drives the dehydrogenation reaction stoichiometrically towards increased dehydrogenation and olefin yield and away from hydrogen saturation.

The dehydrogenation catalyst and process of the present invention can be retrofitted to utilize existing processes and facilities such as, but not limited to those formerly dedicated to naphtha reforming. A catalytic reformer can possess reaction systems and manifolding, furnace hardware, hydrocarbon separation, and catalyst regeneration equipment particularly synergistic to use with the process of the present invention.

BRIEF DESCRIPTION OF THE INVENTION

The hydrocarbon feedstock suitable for use with about the present invention generally comprises paraffinic hydrocarbons having from about 2 to 20 carbon atoms and more preferably from about 2 to 12 carbon atoms for best results. The preferred hydrocarbon feedstock boils at a temperature of below $700°$ F. at atmospheric pressure and more preferably below $450°$ F. at atmospheric pressure.

In one embodiment, the process can be provided for dehydrogenating hydrocarbon for direct or eventual upgrade to ethers such as, but not limited to, MTBE, ETBE, and TAME. Feedstocks for use with the present invention and suitable for providing etherification feedstocks will generally comprise aliphatic or alicyclic hydrocarbon having from 3 to 7 carbon atoms. The preferred feedstocks generally comprise at least 5 weight percent paraffinic hydrocarbon and more preferably at least 10 weight percent paraffinic hydrocarbon to justify the capital and operating costs to perform dehydrogenation. Since most etherification processes convert iso-olefins to ethers, the feedstock to such processes often requires isomerization prior to etherification. The feedstock suitable for use with the present invention can effectively dehydrogenate isoparaffins as well as normal paraffins therefore providing the flexibility to incorporate the process upstream, downstream or concurrent with an isomerization step.

In a second embodiment, the process can be provided for dehydrogenating hydrocarbon for improving gasoline research and/or motor octane. Generally, olefinic hydrocarbon boiling in the gasoline or naphtha boiling point temperature range has a higher research and motor octane than its paraffinic counterparts. At least a portion of such feedstocks will generally comprise paraffinic hydrocarbon having from 4 to 12 carbon atoms and the paraffinic hydrocarbon can be normal, isomeric, or a combination thereof.

In a third embodiment, the process can be provided to dehydrogenate hydrocarbon for feed to a petroleum refinery alkylation process. Feedstocks suitable for dehydrogenation in accordance with the present invention and for providing alkylation unit feedstock preferably comprise paraffinic hydrocarbon having from 3 to 6 carbon atoms and more preferably from 3 to 5 carbon atoms. The paraffinic fraction of the feedstock can be normal, isomeric, or a combination thereof.

In still another embodiment, the process can be provided to dehydrogenate hydrocarbon as feed for commercial chemical manufacture. Feedstocks having from 2 to 4 carbon atoms can be dehydrogenated into olefinic feedstocks for the subsequent production of polyethylene, polypropylene, polybutene, or other chemical compositions that are commonly sold in solid or liquid forms.

The above feedstocks can be processed through the process of the present invention neat or can be combined with recycled portions of the product stream from the dehydrogenation process. Similarly, combinations of the above-described feedstock embodiments can be directed to the process of the present invention and the products subsequently fractionated to individual product pools. The process of the present invention can also be operated in "blocked out" mode where only one feedstock is processed through the facility at any one time. Blocked out operation simplifies processing capital requirements but can also increase tankage capital and inventory holding costs. Other feedstock combinations and methods to comport the process of the present invention to individual needs will be known to those skilled in the art.

The process of the present invention comprises a dehydrogenation catalyst comprising a platinum group metal and zinc on a support component comprising a borosilicate molecular sieve and an alkali metal. The borosilicate molecular sieve-containing support can also comprise an inorganic oxide binder.

The preferred crystalline borosilicate molecular sieves are of the AMS type and have the following composition in terms of mole ratios of oxides:

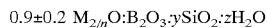

wherein M is at least one cation having a valence of n, y ranges from about 4 to about 600, and z ranges from 0 to about 160, and provide an X-ray diffraction pattern comprising the following X-ray lines and assigned strengths:

| d-Spacing (Å) | Assigned Strength |
|---|---|
| 11.2 ± 0.2 | W–VS |
| 10.0 ± 0.2 | W–MS |
| 5.97 ± 0.07 | W–M |
| 3.82 ± 0.05 | VS |
| 3.70 ± 0.05 | MS |
| 3.62 ± 0.05 | M–MS |
| 2.97 ± 0.02 | W–M |
| 1.99 ± 0.02 | VW–M |

For ease of reporting X-ray diffraction results, relative intensities (relative peak heights) were arbitrarily assigned the following values:

| Relative Peak Height | Assigned Strength |
|---|---|
| less than 10 | VW (very weak) |
| 10–19 | W (weak) |
| 20–39 | M (medium) |
| 40–70 | MS (medium strong) |
| greater than 70 | VS (very strong) |

The preferred borosilicate molecular sieve, by virtue of its superior stability and selectivity, is the AMS-1B type which is in the sodium form as synthesized. The original cation in the AMS-1B crystalline borosilicate molecular sieve, which usually is sodium ion, can be replaced all or in part by ion exchange with other cations including other metal ions and their amino complexes, alkylammonium ions, hydrogen ions, and mixtures thereof. Preferred replacing cations are those which render the crystalline borosilicate molecular sieve catalytically active, particularly for hydrocarbon conversion. Suitable catalytically active ions include hydrogen, metal ions of Groups IB, IIA, IIB, IIIA, VIB, and VIII (IUPAC), and ions of manganese, vanadium, chromium, uranium, and rare earth elements. The preferred form of AMS-1B is the hydrogen form, HAMS-1B, which can be prepared by ammonium exchange followed by calcination. Further details with respect to these crystalline borosilicate molecular sieves can be found in commonly assigned U.S. Pat. No. 4,269,813 to Klotz, which is herein incorporated by reference.

The AMS-1B borosilicate molecular sieve useful in this invention can be prepared by crystallizing an aqueous mixture of cation sources, an oxide of boron, an oxide of silicon, and an organic template compound, at a controlled pH.

Typically, the mole ratios of the various reactants can be varied to produce the crystalline borosilicate molecular sieve of this invention. Specifically, the mole ratios of the initial reactant concentrations are indicated below:

|  | Broad | Preferred | Most Preferred |
|---|---|---|---|
| $SiO_2/B_2O_3$ | 5–400 | 10–150 | 10–80 |
| $R_2O^+/[R_2O^+ + M_{2/n}O]$ | 0.1–1.0 | 0.2–0.97 | 0.3–0.97 |
| $OH^-/SiO_2$ | 0.01–11 | 0.1–2 | 0.1–1 | wherein R is an organic compound and M is a least one cation having a valence n, such as an alkali metal or an alkaline earth metal cation. By regulation of the quantity of boron (represented as $B_2O_3$) in the reaction mixture, it is possible to vary the $SiO_2$ molar ratio in the final product.

More specifically, the material useful in the present invention is prepared by mixing a cation source compound, a boron oxide source, and an organic template compound in water (preferably distilled or deionized). The order of addition is generally not critical although a typical procedure is to dissolve sodium hydroxide and boric acid in water and then add the template compound. Generally, after adjusting the pH, the silicon oxide compound is added, with intensive mixing, such as that performed in a Waring blender. After the pH is checked and adjusted if necessary, the resulting slurry is transferred to a closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of $OH^-/SiO_2$ shown above should furnish a pH of the system that broadly falls within the range of about 9 to about 13.5. Advantageously, the pH of the reaction system falls within the range of about 10.5 to about 11.5 and more preferably between about 10.8 and about 11.2 for best results.

Examples of oxides of silicon useful in this invention include silicic acid, sodium silicate, tetraalkyl silicates, and Ludox, a stabilized polymer of silicic acid manufactured by E. I. DuPont de Nemours & Co. The silica source is preferably a low sodium content silica source containing less than 2,000 ppm sodium and more preferably less than 1000 ppm sodium, such as Ludox HS-40 which contains about 40 wt % $SiO_2$ and 0.08 wt % $Na_2O$ or Nalco 2327 which has similar specifications. The oxide of boron source is generally boric acid although equivalent species can be used such as sodium borate and other boron-containing compounds.

Cations useful in formation of AMS-1B include alkali metal and alkaline earth metal cations such as sodium, potassium, lithium, calcium, and magnesium. Ammonium cations may be used alone or in conjunction with such metal cations. Since basic conditions are required for crystallization of the molecular sieve of this invention, the source of such cation usually is a hydroxide such as sodium hydroxide. Alternatively, AMS-1B can be prepared directly in the hydrogen form by replacing such metal cation with an organic base such as ethylenediamine.

Organic templates useful in preparing AMS-1B crystalline borosilicate molecular sieves include alkylammonium cations or precursors thereof such as tetraalkylammonium compounds. A useful organic template is tetra-n-propylammonium bromide. Diamines, such as hexamethylenediamine, can also be used.

It is noted that the preferable amount of alkylammonium template compound used in the above-described preparation method is substantially less than that required to produce AMS-1B conventionally using an alkali metal cation base.

The crystalline borosilicate molecular sieve prepared by the above-described method typically contains at least 9,000 ppm boron and less than about 100 ppm sodium and is designated as HAMS-1B-3. The HAMS-1B-3 crystalline borosilicate molecular sieve has a higher boron content and a lower sodium content than crystalline borosilicates formed using conventional techniques.

In a more detailed description of a typical preparation of the borosilicate used in the catalyst and process of the present invention, suitable quantities of sodium hydroxide and boric acid ($H_3BO_3$) are dissolved in distilled or deionized water followed by addition of the organic template. The pH may be adjusted between about 11.0±0.2 using a compatible base or acid such as sodium bisulfate or sodium hydroxide. After sufficient quantities of silicic acid polymer (Ludox HS-40) are added with intensive mixing, the pH can again be checked and adjusted to a range of from about 11.0±0.2. The resulting slurry is transferred to a closed crystallization vessel and reacted usually at a pressure of at least the vapor pressure of water for a time sufficient to permit crystallization. This time period generally ranges from about 6 hours to about 20 days, typically from about 1 day to about 10 days, and preferably extends from about 5 days to about 7 days. The temperature for crystallization is generally maintained at from about 212° F. to about 482° F., preferably from about 257° F. to about 392° F., and more preferably at about 329° F. for best results. The crystallizing material can be stirred or agitated as in a rocker bomb. Preferably, the crystallization temperature is maintained below the decomposition temperature of the organic template compound. Samples of material can be removed during crystallization to check the degree of crystallization and determine the optimum crystallization time.

The crystalline material formed can be separated and recovered by well-known means such as by filtration with washing. This material can be mildly dried for anywhere from a few hours to a few days at varying temperatures, typically ranging from about 77° F. to about 392° F., to form a dry cake. The dry cake can then be crushed to a powder or to small particles and extruded, pelletized, or made into forms suitable for its intended use. Typically, materials prepared after mild drying contain the organic template compound and water of hydration with the solid mass and a subsequent activation or calcination procedure is necessary if it is desired to remove this material from the final product. Calcination is generally performed at temperatures ranging from about 500° F. to about 1562° F. and preferably from about 977° F. to about 1112° F. for best results. Extreme calcination temperatures or prolonged crystallization times may prove detrimental to the crystal structure or may destroy it. Generally there is minimal benefit in raising the calcination temperature beyond about 1112° F. in order to remove organic material from the originally formed crystalline material. The molecular sieve material can then be dried in a forced draft oven at about 329° F. for about 16 hours prior to calcination in air in a manner such that the temperature rise does not exceed 225° F. per hour. Once a temperature of about 1000° F. is reached, calcination temperature is generally maintained for about an additional 4 to 16 hours.

The dehydrogenation metals in accordance with the present invention generally include a zinc component in combination with one or more platinum group metals.

The zinc component can be present in its elemental form or as its oxide, sulfide, or mixtures thereof. The zinc component is generally present in the dehydrogenation catalyst in an amount ranging from about 0.02 weight percent to about 10.0 weight percent, preferably from about 0.1 weight percent to about 5.0 weight percent, and more preferably from about 1.0 weight percent to about 4.0 weight percent based on the total weight of the dehydrogenation catalyst and calculated as oxide, for best results.

The platinum group metal component can include one or more of the platinum group metals, preferably platinum or palladium, and more preferably platinum for best results. The platinum group metals can be present in the dehydrogenation catalyst in their elemental form or as their oxides, sulfides, or mixtures thereof. The platinum group metals are cumulatively present in an amount ranging from about 0.01 weight percent to about 5.0 weight percent, preferably from about 0.1 weight percent to about 3.0 weight percent, more preferably from about 0.1 weight percent to about 2.0 weight percent, and most preferably from about 0.1 weight percent to about 1.5 weight percent based on the total weight of the catalyst and calculated as oxide, for best results.

Catalyst dehydrogenation metals concentrations outside of the above-described zinc and cumulative platinum group metals ranges are generally less economic. Higher metals concentrations can require more total dehydrogenation metal component due to reduced dispersion and hydrocarbon/catalyst contact. Lower metals concentration can result in increased support material requirements, catalyst handling, transportation, and capital costs.

The zinc and platinum group dehydrogenation metal components can be deposed or incorporated upon the support component by impregnation employing heat-decomposable salts of the zinc and platinum group metals or through other methods known to those skilled in the art such as ion-exchange, with impregnation methods being preferred. The zinc and platinum group metals can be impregnated onto the support separately, or can be co-impregnated onto the support. Suitable aqueous impregnation solutions include, but are not limited to, zinc nitrate, zinc chloride, chloroplatinic acid, palladium chloride, tetraamine palladium chloride, and tetraamine platinum chloride.

Impregnation using an mpregnation solution comprising zinc nitrate and tetraamine platinum chloride can be performed by precalcining the dehydrogenation support component, in the form of a powder, pellets, extrudates, or spheres and determining the amount of water that must be added to wet all of the material. The zinc nitrate and tetraamine platinum chloride are then dissolved in the calculated amount of water, and the solution added to the support in a manner such that the solution completely saturates the support. The zinc nitrate and tetraamine platinum chloride are added in a manner such that the aqueous solution contains the total amount of elemental zinc and platinum to be deposited on the given mass of support. Impregnation can be performed for each metal separately, including an intervening drying step between impregnations, or as a single co-impregnation step. The saturated support is then generally separated, drained, and dried in preparation for calcining. Commercially, draining volumes can be reduced in order to reduce zinc and platinum losses and waste water handling costs by providing less than the full amount of aqueous solution (such as from 90% to 100% by volume of aqueous solution) necessary to saturate all of the support. Calcination generally is performed at a temperature of from about 600° F. to about 1,202° F. (315° C. to about 650° C.), or more preferably from about 700° F. to about 1,067° F. (371° C. to about 575° C.) for best results.

It has been found that combining zinc and platinum group metal components in accordance with the present invention provides substantially improved dehydrogenation stability resulting in longer catalyst cycles between regenerations and extended overall catalyst life before replacement. The zinc and platinum group metals can be added to the catalyst of the present invention in zinc to platinum group weight ratios extending from 10:1 to 1:10, preferably from 7:1 to 1:7, and most preferably from 7:1 to 1:1 for best results.

It has also been found that during dehydrogenation operation in accordance with the present invention, post-analysis of the catalyst after significant hours on stream can show significant reductions in zinc concentration on the catalyst to levels as low as 50 percent, 25 percent, and even 15 percent of the level of the originally impregnated catalyst. This is believed to be true due to volatilization of the impregnated zinc component during dehydrogenation operations where operating temperatures can often exceed 1000° F. While the zinc concentrations and therefore the zinc to platinum ratio tend to be reduced with on stream time, the catalyst performance is generally not substantially effected. Zinc volatilization can be managed by post incorporation of zinc after a regeneration cycle or by addition of a Group IVB metal such as zirconium during initial catalyst formulation.

The dehydrogenation catalyst in accordance with the present invention can and generally comprises various binders or matrix materials depending on the intended process use. The base catalyst can be combined with active or inactive materials, synthetic or naturally-occurring zeolites, as well as inorganic or organic materials which would be useful for binding the borosilicate. Well-known materials include silica, silica-alumina, alumina, alumina sols, hydrated aluminas, clays such as bentonite or kaolin, or other binders known in the art.

Silica is the preferred binder for use with the dehydrogenation catalyst of the present invention. Dehydrogenation catalysts in accordance with the present invention and having silica binders are generally preferable to alternative binders in that they do not generally affect overall catalyst acidity in contradistinction to binders such as alumina and other metal oxides commonly used in catalysis.

The borosilicate molecular sieve component is generally present in the dehydrogenation catalyst of the present invention in an amount ranging from about 5.0 weight percent to about 98.0 weight percent, preferably from about 20.0 weight percent to about 80.0 weight percent, and more preferably from about 40.0 weight percent to about 60.0 weight percent for best results. Crystalline borosilicate molecular sieve component concentrations as a percentage of the dehydrogenation catalyst, in a range of from about 40.0 weight percent to about 60.0 weight percent, are particularly preferred because it has been found, that these levels promote an optimum balance of paraffin conversion and olefin selectivity for producing maximum volume yields of the desired olefins. Higher percentages of the borosilicate molecular sieve component can result in a softer and less attrition resistant dehydrogenation catalyst which can reduce catalyst life and increase catalyst costs. Lower percentages of the borosilicate molecular sieve component can result in larger catalytic reactor size requirements.

Methods for dispersing the base catalyst comprising the borosilicate molecular sieve and dehydrogenation metal components in accordance with the present invention within a refractory inorganic oxide matrix component are generally well-known to persons skilled in the art. A preferred method is to blend the base catalyst component, preferably in a finely divided form, into a sol, hydrosol, or hydrogel of an inorganic oxide, and then add a gelling medium such as ammonium hydroxide to the blend with stirring to produce a gel. The resulting gel can be dried, dimensionally formed if desired, and calcined. Drying is preferably conducted in air at a temperature of about 80° F. to about 350° F. (about 27° C. to about 177° C.) for a period of several seconds to several hours. Calcination is preferably conducted by heating in air at about 932° F. to about 1202° F. (about 500° C. to about 650° C.) for a period of time ranging from about 0.5 hours to about 16 hours.

Another suitable method for preparing a dispersion of a base catalyst in a refractory inorganic oxide matrix component is to dry blend particles of each, preferably in finely divided form, and then to dimensionally form the dispersion if desired.

The dehydrogenation catalyst support component also comprises a particularly targeted alkali metal concentration, calculated as a percentage by weight of the dehydrogenation catalyst. The preferred alkali metals are potassium and sodium with sodium being most preferred. The alkali metal concentration of the dehydrogenation catalyst in accordance with the present invention generally ranges from about 0.1 weight percent to about 10.0 weight percent, calculated as a percentage of the dehydrogenation catalyst, preferably from about 0.5 weight percent to about 7.0 weight percent, and more preferably from about 1.0 weight percent to about 4.0 weight percent for best results.

It has been found that a dehydrogenation process using a comparable dehydrogenation catalyst, but with an alkali metal concentration below the ranges set forth above, can result in substantial reductions in olefin selectivity which generally overwhelm small paraffin conversion increases, resulting in lower olefin yields and inferior dehydrogenation performance. Alkali metal concentration above the ranges set forth above, can result in reductions in paraffin conversion that overwhelm diminishing marginal benefits in olefin selectivity, thereby resulting in lower olefin yields and inferior dehydrogenation performance.

Where the alkali metal concentration of the support comprising a borosilicate molecular sieve would result in a dehydrogenation catalyst having an alkali metal concentration above the particularly targeted concentration range described above, the alkali metal is generally removed by replacement of the alkali metal with ammonium ions followed by decomposition of the ammonium form by calcination.

Where the alkali metal concentration of the support comprising a borosilicate molecular sieve is below the particularly targeted alkali metal concentration, the alkali metal is generally back-added to the support by impregnation employing the heat-decomposable salts of the alkali metal or by other methods known to those skilled in the art such as ion-exchange, with impregnation being preferred. Suitable aqueous sodium impregnation solutions can include, but are not limited to sodium nitrate and sodium acetate.

Impregnation, such as with sodium, using sodium nitrate or sodium acetate, can begin by precalcining the support component in preparation for using incipient wetness techniques. Under conventional incipient wetness techniques, a determination is generally made as to the amount of water required to saturate and fill the pores of the support component. A solution is then prepared utilizing the predetermined amount of water and a sufficient amount of the sodium salt to provide a dehydrogenation catalyst having the desired concentration of sodium. The impregnated support component is then separated, drained, and dried in preparation for calcining. Calcination is generally performed at a temperature ranging from about 600° F. to about 1,202° F., and preferably from about 700° F. to about 1067° F.

The dehydrogenation process of the present invention can begin with a hydrocarbon feedstock preheating step. The feedstock can be preheated in feed/reactor effluent heat exchangers prior to entering a furnace or contacting other high temperature waste heat means for final preheating to a targeted catalytic reaction zone inlet temperature. Suitable final preheating means can include, but are not limited to waste heat from other refinery processes such as a fluid catalytic cracking unit, a fluidized or delayed coking unit, a catalytic hydrocracker, a crude distillation unit, a catalytic reforming unit, and/or hydrotreating units found in conventional petroleum refineries.

The feedstock can be contacted with a hydrogen stream prior to, during, and/or after preheating, before the catalytic dehydrogenation reaction zone, in any one or more of the reactors in the reaction zone, or between reactors in a multiple reactor reaction zone. The process may also be operated in the substantial absence of supplemental hydrogen addition. A fundamental and invaluable aspect of the present invention is that the subject dehydrogenation catalyst can be effectively utilized without the addition of supplemental hydrogen in addition to that inherently released through the dehydrogenation reaction. The addition of supplemental hydrogen in the process can reduce the rate of catalyst deactivation, resulting in reduced catalyst regeneration requirements. However, hydrogen addition may also adversely affect olefin yield by directing the reaction stoichiometrically away from dehydrogenation and toward olefin saturation.

Where a supplemental hydrogen stream is added, the hydrogen stream can be pure hydrogen or can be in admixture with diluents such as low-boiling hydrocarbons, carbon monoxide, carbon dioxide, nitrogen, water, sulfur compounds, and the like. The hydrogen stream purity should be at least about 50% by volume hydrogen, preferably at least about 65% by volume hydrogen, and more preferably at least about 75% by volume hydrogen for best results. Hydrogen can be supplied from a hydrogen plant, a catalytic reforming facility, or other hydrogen-producing or hydrogen-recovery processes.

The reaction zone can include, but is not limited to, one or more fixed bed reactors containing the same or different catalysts, a moving column reactor and catalyst regeneration system, or a fluidized bed reactor and regenerator, with a fixed bed reactor process being preferred. The feedstock may be contacted with a catalyst or a catalyst bed in either upward, downward, or radial flow fashion with downflow being preferred. The reactants may be in the liquid phase, admixed liquid and vapor phase, or the vapor phase, with the best results obtained in the vapor phase.

Moving column reactors and regenerator systems such as that described in U.S. Pat. No. 3,647,680 to Greenwood et al. are known in the art and commonly used in processes such as catalytic reforming. The system generally comprises a vertical elongated reaction vessel comprising moving annular columns of catalyst wherein hydrocarbon is passed in out-to-in radial flow towards the center of the reaction vessel. Portions of the moving bed of catalyst are continuously directed to a regeneration system for regenerating the catalyst through combustion of coke components.

Fluidized bed reactors, which are commonly used in fluidized catalytic cracking and fluidized coking processes, fluidize the catalyst directly within the hydrocarbon feedstock, separate the catalyst from the reaction products, and direct the spent catalyst back to a regeneration zone for regeneration. The heat of reaction from the burning of coke from the catalyst generally supplies the heat requirements for sustaining the particular process reactions.

The preferred reaction zone facilities for use with the dehydrogenation process of the present invention are fixed bed reactors. It is preferred that the dehydrogenation reaction zone comprise at least two fixed bed reactors so as to facilitate on stream regeneration of the catalyst. The fixed bed reactors are generally equipped with proper manifolding to permit removal of each reactor from operation in a manner so as to provide for regeneration of the catalyst in that reactor while the other reactor or reactors sustain process operations. Fixed bed reactors in accordance with the present invention can also comprise a plurality of catalyst beds. The plurality of catalyst beds in a single fixed bed reactor can also comprise the same or different catalysts.

Since the dehydrogenation reaction is generally endothermic, interstage heating, consisting of heat transfer devices between fixed bed reactors or between catalyst beds in the same reactor shell, can be employed. Heat sources can include conventional process heaters such as one or more process furnaces or can include internally produced heat such as that produced from catalyst regeneration within a fluidized catalytic process. Heating requirements may also be met from heating sources available from other refinery process units such as from a fluid catalytic cracking process or a fluidized coker. Multiple reactor processes can provide reduced temperature endotherm per reactor shell and more effective temperature control but generally cost more in terms of capital requirements.

The dehydrogenation reaction zone effluent is generally cooled and the effluent stream is directed to a separator device such as a stripper tower where light hydrocarbons and hydrogen formed during the reaction step can be removed and directed to more appropriate hydrocarbon pools. Where the process is performed in the presence of supplemental hydrogen or sufficient internally generated hydrogen is produced, a separate hydrogen separation step can be performed upstream of and prior to light hydrocarbon separation. Some of the recovered hydrogen can be recycled back to the process while some of the hydrogen can be purged to external systems such as plant or refinery fuel. The hydrogen purge rate can be controlled to maintain minimum hydrogen purity. Recycled hydrogen can be compressed, supplemented with "make-up" hydrogen, and reinjected into the process for further dehydrogenation where supplemental hydrogen is added.

The stripper liquid effluent product is then generally conveyed to downsteam processing facilities. The olefin product can be directed to an isomerization process for isomerization and thereafter directed to an ether facility for conversion, in the presence of alkanol, to an ether. Where at least a portion of the olefin from the process of the present invention is iso-olefin, the stream can be sent directly to an ether facility. Prior to direction to an ether facility, the product stream can be purified by removing unconverted paraffinic hydrocarbon from the product. This unconverted product can be recycled back to the reaction zone or further manipulated in other process units. The olefin product can be directed to an alkylation process for reaction with isoparaffin to form higher octane, lower volatility gasoline blending components. The olefin product can be directed to a chemical manufacture process for conversion to other commodity chemical products or process streams. Methods for integration of the process of the present invention with other conventional refinery or chemical plant processes or products will be generally known to those skilled in the art.

Notwithstanding the superior stability properties of the dehydrogenation catalyst of the present invention, periodic catalyst regeneration may be required depending on the severity of operation and other process parameters. It is anticipated that the catalyst utilized in the process of the present invention may require regeneration as often as once every 6 months, as often as once every 3 months, and, on occasion, as often as once or twice every month. The dehydrogenation catalyst of the present invention is particularly suited for regeneration by the oxidation or burning of catalyst deactivating carbonaceous deposits with oxygen or an oxygen-containing gas. Moreover, catalyst performance is not generally diminished from periodic regeneration, in contradistinction to comparison catalysts tested. The term "regeneration," for purposes of the present invention, shall mean the recovery of at least a portion of the molecular sieve initial activity by combusting the coke deposits on the catalyst with oxygen or an oxygen-containing gas.

The prior art is replete with catalyst regeneration techniques that may be employed in the process of the present invention. Some of these regeneration techniques involve chemical methods for increasing the activity of deactivated molecular sieves. Others, including the preferred methods, relate to processes or methods for regenerating carbon (also known as coke) deactivated catalysts by the combustion of the coke with an oxygen-containing gas stream.

For example, U.S. Pat. No. 2,391,327 discloses the regeneration of catalysts contaminated with carbonaceous deposits with a cyclic flow of regeneration gases.

U.S. Pat. No. 3,755,961 relates to the regeneration of coke-containing crystalline zeolite molecular sieves which have been employed in an absorptive hydrocarbon separation process. The process involves the continuous circulation of an inert gas containing a quantity of oxygen in a closed loop arrangement through the bed of molecular sieve.

U.S. Pat. No. 4,480,144 relates to the use of a circulating gas to regenerate a coke deactivated zeolite-containing catalyst. The circulating gas is maintained at a low moisture level by purging wet gases from the loop while simultaneously introducing dry gases into the loop. This method is particularly useful with zeolitic catalysts since zeolitic catalysts can be detrimentally effected by the presence of water.

The conditions and methods at which a catalyst may be regenerated by coke combustion can vary. It is typically desired to perform coke combustion at conditions of temperature, pressure, gas space velocity, etc. which are least damaging thermally to the catalyst being regenerated. It is also desired to perform the regeneration in a timely manner to reduce process down-time in the case of a fixed bed reactor system or equipment size, in the case of a continuous regeneration process.

Optimum regeneration conditions and methods are generally disclosed in the prior art as mentioned hereabove. Catalyst regeneration is typically accomplished at conditions including a temperature range of from about 550° F. to about 1300° F., a pressure range of from about 0 psig to about 300 psig, and a regeneration gas oxygen content of from about 0.1 mole percent to about 23.0 mole percent. The oxygen content of the regeneration gas is typically increased during the course of a catalyst regeneration procedure based on catalyst bed outlet temperatures, in order to regenerate the catalyst as quickly as possible while avoiding catalyst-damaging process conditions.

The preferred catalyst regeneration conditions include a temperature ranging from about 600° F. to about 1150° F., a pressure ranging from about 0 psig to about 150 psig, and a regeneration gas oxygen content of about 0.1 mole percent to about 10 mole percent for best results.

Additionally, it is important that regeneration be accomplished in the presence of an oxygen-containing gas. The oxygen-containing regeneration gas typically comprises nitrogen and carbon combustion products such as carbon monoxide and carbon dioxide, to which oxygen in the form of air has been added. However, it is possible that the oxygen can be introduced into the regeneration gas as pure oxygen, or as a mixture of oxygen diluted with another gaseous component. Air is the preferred oxygen-containing gas.

Operating conditions to be used in the dehydrogenation process of the present invention include an average catalytic reaction zone temperature of from about 500° F. to about 1300° F., preferably from about 700° F. to about 1200° F., and more preferably from about 850° F. to about 1100° F. for best results. Reaction temperatures below these ranges can result in reduced paraffin conversion and lower olefin yield. Reaction temperatures above these ranges can result in reduced olefin selectivity and lower olefin yields.

The process of the present invention generally operates at catalytic reaction zone pressures ranging from as low as substantially vacuum pressure (about 0 to about 27.6 inches of water vacuum) to about 500 psig, preferably from about vacuum pressure to about 300 psig, and more preferably from about vacuum pressure to about 100 psig for best results. Where the process operates in the presence of hydrogen, hydrogen circulation rates generally range from about 1 SCF/Bbl to about 12,000 SCF/Bbl, preferably from about 1 SCF/Bbl to about 6,000 SCF/Bbl, and most preferably from about 1 SCF/Bbl to about 1,000 SCF/Bbl for best results. Reaction pressures and hydrogen circulation rates below these ranges can result in higher catalyst deactivation rates resulting in increased energy intensive regeneration cycles. Excessively high reaction pressures increase energy and equipment costs and provide diminishing marginal benefits. Excessively high hydrogen circulation rates can also influence reaction equilibrium and drive the reaction undesirably towards reduced paraffin conversion and lower olefin yield.

The process of the present invention generally operates at a weight hourly space velocity (WHSV) of from about 0.1 $hr^{-1}$ to about 100 $hr^{-1}$, preferably from about 0.5 $hr^{-1}$ to about 40 $hr^{-1}$, and most preferably from about 0.5 $hr^{-1}$ to about 20 $hr^{-1}$ for best results. Feed space velocities exceeding the levels described herein generally result in a decline in paraffin conversion which overwhelm any gain in olefin selectivity, thereby resulting in lower olefin yield. Feed space velocities short of the levels described herein are generally costly in terms of capital requirements.

The dehydrogenation catalyst and process of the present invention provides superior overall dehydrogenation properties closely approaching thermodynamic equilibrium. The dehydrogenation catalyst of the present invention can reach paraffin conversion levels in excess of 25 percent, typically in excess of 35 percent, and commonly in excess of 40 percent. Olefin selectivity levels are generally maintained in excess of 80 percent, typically in excess of 85 percent, and commonly exceed 90 percent. These levels of paraffin conversion and olefin selectivity result in olefin yield levels which generally exceed 25 percent, typically exceed 35 percent, and commonly exceed 40 percent.

The dehydrogenation catalyst and process of the present invention provides the above-described levels of performance while resisting catalyst deactivation, thereby extending catalyst cycle life under dehydrogenation conditions. The dehydrogenation catalyst of the present invention can and has achieved olefin yield deactivation loss levels of 0.6 percent per day or less at a reaction temperature of 1050° F. At reaction temperatures of 1075° F., the dehydrogenation catalyst of the present invention has maintained olefin yield deactivation loss at levels of 1.1 percent conversion or lower. The catalyst of the present invention has operated with negligible olefin yield loss (and actually a slight increase) over an on stream period in excess of 1100 hours with only 3 regenerations. During this scenario, paraffin conversion actually increased at a rate in excess of the rate of loss of olefin selectivity, resulting in an actual increase in olefin yield.

The dehydrogenation catalyst and process of the present invention can be utilized for on stream periods in excess of 120 hours, 310 hours, 400 hours, and even in excess of one to several months at a reaction temperature of 1000° F. before requiring catalyst regeneration or replacement. As deactivation levels increase over time on stream, olefin selectivity may be reduced, thereby resulting in lower olefin yield and necessitating increased reaction temperatures. Increasing reaction temperatures to maintain olefin yield levels generally accelerate the deactivation process.

The dehydrogenation catalyst and process of the present invention are so effective with regard to catalyst stability and deactivation resistance that the catalyst can be operated in the absence of supplemental hydrogen addition. This is an extraordinary advantage of the process of the present invention for several reasons. Operating in the absence of supplemental hydrogen addition can avoid enormous capital and operating costs connected to the installation and operation of hydrogen recovery facilities which generally include hydrogen gas compressors and separation facilities such as high pressure process towers and membranes. Operating in the absence of supplemental hydrogen also favorably drives the dehydrogenation reaction stoichiometrically towards dehydrogenation and away from hydrogen saturation, in contradistinction to the prior art dehydrogenation processes which generally must be conducted in the presence of supplemental hydrogen addition in order to maintain a viable catalyst run length.

The dehydrogenation catalyst and process of the present invention can be retrofitted to utilize existing processes and facilities such as, but not limited to, those previously dedicated to naphtha reforming. The reaction pressure requirements are generally low and therefore, suitable reactor vessels may be located from any of several sources. A catalytic reformer may also possess furnace hardware, hydrocarbon separation, and catalyst regeneration equipment particularly synergistic to use with the process of the present invention. Catalytic reforming is also particularly suited for retrofit with the present invention in view of recent environmental mandates to produce gasolines containing lower aromatic concentrations (a fundamental product of catalytic reforming).

The present invention is described in further detail in connection with the following examples, it being understood that the same are for purposes of illustration and not limitation.

EXAMPLE 1

A paraffin dehydrogenation catalyst in accordance with the present invention and comprising about 57.50 percent by weight of a borosilicate molecular sieve, 38.30 percent by weight of a silica binder, 2.10 percent by weight of sodium, 1.78 percent by weight of zinc, and about 0.32 percent by weight of platinum was prepared for comparison with catalysts not in accordance with the present invention.

The dehydrogenation catalyst was prepared by, first synthesizing a quantity of an ammonium exchanged HAMS-1B-3 borosilicate molecular sieve in a manner similar to that described in European Patent No. 0184461 to Haddad et al. and U.S. Pat. No. 4,725,570 to Haddad et al., the disclosures of which are hereby incorporated by reference.

The dehydrogenation catalyst was prepared by incipient wetness impregnation of 25.0 grams of the ammonium exchanged HAMS-1B-3 borosilicate molecular sieve with a solution containing 2.7 grams of zinc acetate (Zn $(OOCCH_3.2H_2O)$) and 30.0 grams of water. The zinc impregnated borosilicate molecular sieve was dried and calcined in air at 1000° F. for a period of 6 hours. The calcined particulate was impregnated using incipient wetness techniques with a solution containing 0.22 grams of platinum tetraamine nitrate ($Pt(NH_3)_4(NO_3)_2$) and 30.0 grams of distilled water. The platinum and zinc impregnated borosilicate molecular sieve was dried and 20.7 grams of the dried particulate mixed with 13.8 grams of CAB-O-SIL EH-5 silica (manufactured By Cabot Corporation) and 100.0 grams of distilled water in a small Waring blender for a period of 5 to 10 minutes. The mixture was dried at 250° F. for 16 hours in a forced air oven, crushed, and sized to 12 to 20,mesh (U.S. Sieve Series). The crushed and sized base catalyst (23.3 grams) was further impregnated with a solution containing 1.7 grams of sodium nitrate and 22.0 grams of distilled water and dried. The catalyst was designated as Catalyst 1. The properties of the HAMS-1B-3, the CAB-0-SIL EH-5 silica, and Catalyst 1 are provided in Table 1.

TABLE 1

| Catalyst | Na, Pt, Zn/HAMS-1B-3 | HAMS-1B-3 | CAB-O-SIL EH-5 Silica |
|---|---|---|---|
| % Sieve | 57.50 | 99.92 | — |
| % SiO$_2$ | 38.30 | — | 100 |
| % Pt | 0.32 | — | — |
| % Zn | 1.78 | — | — |
| % Na | 2.10 | 0.08 | — |
| % Crystallinity | 48 | 95 | — |
| BET SA, m$^2$/g | 277 | 317 | 339 |
| Cum Pore Vol, cc/g | 0.78 | 0.07 | 1.23 |
| Micropore Area, m$^2$/g | 142 | 278 | 12 |
| Micropore Vol, cc/g | 0.065 | 0.125 | 0.006 |

EXAMPLE 2

A comparison paraffin dehydrogenation catalyst similar to Catalyst 1 but without back-added sodium was prepared for comparison with the dehydrogenation catalyst in accordance with the present invention. The comparison catalyst comprised about 58.7 percent by weight of a borosilicate molecular sieve, 39.2 percent by weight of a silica binder, 1.8 percent by weight of zinc, and about 0.3 percent by weight of platinum.

The dehydrogenation catalyst was prepared by first synthesizing a quantity of an ammonium exchanged HAMS-1B-3 borosilicate molecular sieve in a manner similar to that described for Catalyst 1. The dehydrogenation catalyst was prepared by incipient wetness impregnation of 25.0 grams of the ammonium exchanged HAMS-1B-3 borosilicate molecular sieve with a solution containing 2.7 grams of zinc acetate (Zn(OOCCH$_3$.2H$_2$O)) and 30.0 grams of water. The zinc impregnated borosilicate molecular sieve was dried and calcined in air at 1000° F. for a period of 6 hours. The calcined particulate was impregnated using incipient wetness techniques with a solution containing 0.22 grams of platinum tetraamine nitrate (Pt(NH$_3$)$_4$(NO$_3$)$_2$) and 30.0 grams of distilled water. The platinum and zinc impregnated borosilicate molecular sieve was dried and 20.7 grams of the dried particulate mixed with 13.8 grams of CAB-O-SIL EH-5 silica and 100.0 grams of distilled water in a small Waring blender for a period of 5 to 10 minutes. The mixture was dried at 250° F. for 16 hours in a forced air oven, crushed, and sized to 12 to 20 mesh (U.S. Sieve Series). The catalyst was designated as Catalyst 2.

EXAMPLE 3

A comparison paraffin dehydrogenation catalyst similar to Catalyst 1 but without zinc was prepared for comparison with the dehydrogenation catalyst in accordance with the present invention. The comparison catalyst comprised about 58.6 percent by weight of a borosilicate molecular sieve, 39.1 percent by weight of a silica binder, 2.0 percent by weight of sodium, and about 0.3 percent by weight of platinum.

The dehydrogenation catalyst was prepared by first synthesizing a quantity of an ammonium exchanged HAMS-1B-3 borosilicate molecular sieve in a manner similar to that described for Catalyst 1. The dehydrogenation catalyst was prepared by incipient wetness impregnation of 25.0 grams of the ammonium exchanged HAMS-1B-3 borosilicate molecular sieve with a solution containing 0.22 grams of platinum tetraamine nitrate (Pt(NH$_3$)$_4$(NO$_3$)$_2$) and 30.0 grams of distilled water. The platinum impregnated borosilicate molecular sieve was dried and 20.0 grams of the dried particulate mixed with 13.3 grams of CAB-O-SIL EH-5 silica and 100.0 grams of distilled water in a small Waring blender for a period of 5 to 10 minutes. The mixture was dried at 250° F. for 16 hours in a forced air oven, crushed, and sized to 12 to 20 mesh (U.S. Sieve Series). The crushed and sized base catalyst (20.0 grams) was further impregnated with a solution containing 1.5 grams of sodium nitrate and 19.0 grams of distilled water and dried. The catalyst was designated as Catalyst 3.

EXAMPLE 4

A comparison paraffin dehydrogenation catalyst similar to Catalyst 1 but with a sodium-containing alumina support in lieu of a sodium, borosilicate, and silica-containing support was prepared for comparison with the dehydrogenation catalyst in accordance with the present invention. The comparison catalyst comprised about 95.9 percent by weight of an alumina support, 2.0 percent by weight of sodium, 1.8 percent by weight of zinc, and about 0.3 percent by weight of platinum.

The dehydrogenation catalyst was prepared by incipient wetness impregnation of 138.0 grams of Versal 450 Alumina, manufactured by LaRoche Chemicals, with a solution containing 10.1 grams of zinc acetate (Zn (OOCCH$_3$.2H$_2$O)) and 97.0 grams of water. The zinc impregnated alumina was dried and calcined in air at 1000° F. for a period of 3 hours. The calcined particulate (40.0 grams) was impregnated using incipient wetness techniques with a solution containing 0.40 grams of platinum tetraamine nitrate (Pt(NH$_3$)$_4$(NO$_3$)$_2$) and 40.0 grams of distilled water. The platinum and zinc impregnated alumina was dried and 40.0 grams of the dried particulate mixed with a solution containing 2.9 grams of sodium carbonate and 40.0 grams of distilled water. The zinc, platinum, and sodium impregnated alumina was dried and 30.0 grams of the particulate mixed with 15.0 grams of distilled water and compacted into 2 inch pellets. The pellets were dried, crushed, and sized to 12 to 20 mesh (U.S. Sieve Series). The catalyst was designated as Catalyst 4.

EXAMPLE 5

A comparison paraffin dehydrogenation catalyst similar to that disclosed in U.S. Pat. No. 4,438,288 to Imai et al. (i.e. platinum, tin, and alkali or alkaline earth metals on an alumina support) was prepared for comparison with the dehydrogenation catalyst in accordance with the present invention. The comparison catalyst comprised about 96.8 percent by weight of an alumina support, 1.8 percent by weight of sodium, 1.2 percent by weight of tin, and about 0.3 percent by weight of platinum.

The dehydrogenation catalyst was prepared by incipient wetness impregnation of 70.0 grams of Versal 450 Alumina, manufactured by LaRoche Chemicals, with a solution containing 2.3 grams of tin (II) 2-ethylhexanoate (Sn (OOCC$_7$H$_{15}$)$_2$) and 37.0 grams of n-hexane. The tin impregnated alumina was dried and calcined in air at 1000° F. for a period of 3 hours. The calcined particulate (51.4 grams) was impregnated using incipient wetness techniques with a solution containing 0.31 grams of platinum tetraamine nitrate ($Pt(NH_3)_4(NO_3)_2$) and 50.0 grams of distilled water. The platinum and tin impregnated alumina was dried and 50.0 grams of the dried particulate mixed with a solution containing 3.7 grams of sodium carbonate and 50.0 grams of distilled water. The tin, platinum, and sodium impregnated alumina was dried and 33.0 grams of the particulate mixed with 17.0 grams of distilled water and compacted into 2 inch pellets. The pellets were dried, crushed, and sized to 12 to 20 mesh (U.S. Sieve Series). The catalyst was designated as Catalyst 5.

EXAMPLE 6

A feedstock containing 99.5 weight percent isobutane was dehydrogenated over dehydrogenation Catalysts 1–5 from Examples 1–5. All catalysts were tested using a quartz bench-top reactor unit having a quartz tube reactor containing a packed bed. Operation was downflow with once-through hydrocarbon flow. Catalysts of 12 to 20 mesh size (U.S. Sieve Series) were used for testing and the catalysts were positioned between a top and bottom bed of 30 to 50 mesh size (U.S. Sieve Series) alpha alumina. All catalysts were activated by heating under a hydrogen flow from room temperature to 900° F. at a heating rate of 55° F./hour, held for 2 hours at 900° F., and then heated to 1000° F. under a nitrogen purge. The isobutane feedstock was processed through the quartz bench-top unit at varied experimental run lengths. All dehydrogenation reactions were conducted at a pressure of less than 1 psig. Gaseous products were analyzed on a Carle Refinery Gas Analyzer gas chromatograph.

The Catalyst testing conditions, product composition, and performance criteria in terms of isobutane conversion, isobutylene selectivity, and isobutylene yield (defined hereabove) were determined for ascending time on stream. The dehydrogenation results for Catalysts 1–5 are set forth in Tables 2–6.

Deactivation rates for Catalysts 1–5 in terms of conversion loss per day were calculated based on development of a regression line of the isobutylene yield data presented in Tables 2–6. The slope of the line was calculated from the regressed line for each of Catalysts 1–5 and is presented in Table 7 as the percent of initial conversion loss per day through deactivation.

TABLE 2

| Process Conditions | | | | | | | | | | |
|---|---|---|---|---|---|---|---|---|---|---|
| Temperature, ° F. | 1003 | 1003 | 1003 | 1004 | 1004 | 1005 | 1005 | 1004 | 1003 | 1004 |
| Isobutane WHSV, $hr^{-1}$ | 2.9 | 2.9 | 2.9 | 2.9 | 2.9 | 2.9 | 2.9 | 2.9 | 2.9 | 2.9 |
| Time on Stream, hrs | 4.2 | 7.1 | 24.9 | 32.3 | 47.8 | 55.5 | 73.1 | 79.8 | 95.4 | 121.2 |
| Product Composition (mol %) | | | | | | | | | | |
| Hydrogen | 28.06 | 28.32 | 28.07 | 28.26 | 28.11 | 27.77 | 27.95 | 27.45 | 27.54 | 28.24 |
| Methane | 0.75 | 0.73 | 0.63 | 0.60 | 0.55 | 0.54 | 0.52 | 0.50 | 0.47 | 0.43 |
| Ethane | 0.17 | 0.15 | 0.09 | 0.08 | 0.07 | 0.06 | 0.05 | 0.05 | 0.04 | 0.04 |
| Ethylene | 0.00 | 0.00 | 0.00 | 0.00 | 0.00 | 0.00 | 0.00 | 0.00 | 0.00 | 0.00 |
| Propane | 0.54 | 0.41 | 0.36 | 0.34 | 0.37 | 0.20 | 0.44 | 0.45 | 0.52 | 0.39 |
| Propylene | 0.28 | 0.18 | 0.19 | 0.18 | 0.17 | 0.14 | 0.15 | 0.17 | 0.46 | 0.07 |
| Butane | 0.66 | 0.65 | 0.62 | 0.63 | 0.64 | 0.66 | 0.67 | 0.69 | 0.71 | 0.71 |
| Isobutane | 41.77 | 41.99 | 43.35 | 43.31 | 43.40 | 43.57 | 43.33 | 43.37 | 43.10 | 42.81 |
| 2-Butenes | 0.36 | 0.39 | 0.38 | 0.34 | 0.38 | 0.36 | 0.36 | 0.37 | 0.36 | 0.37 |
| 1,3-Butadiene | 0.01 | 0.01 | 0.01 | 0.01 | 0.01 | 0.01 | 0.01 | 0.01 | 0.01 | 0.01 |
| Isobutylene + 1-Butene | 27.40 | 27.17 | 26.34 | 26.25 | 26.33 | 26.69 | 26.52 | 26.94 | 26.79 | 26.93 |
| C5= | 0.00 | 0.00 | 0.00 | 0.00 | 0.00 | 0.00 | 0.00 | 0.00 | 0.00 | 0.00 |
| Results | | | | | | | | | | |
| Isobutane Conv. (%) | 41.94 | 41.42 | 39.73 | 39.63 | 39.63 | 39.68 | 39.86 | 40.21 | 40.52 | 40.34 |
| Isobutylene Sel. (%) | 90.82 | 91.50 | 92.16 | 92.34 | 92.42 | 93.14 | 92.32 | 92.35 | 91.25 | 93.02 |
| Isobutylene Yld. (%) | 38.09 | 37.90 | 36.62 | 36.59 | 36.63 | 36.96 | 36.80 | 37.13 | 36.97 | 37.53 |

| Process Conditions | | | | | | | | | | |
|---|---|---|---|---|---|---|---|---|---|---|
| Temperature, ° F. | 1005 | 1050 | 1050 | 1050 | 1050 | 1050 | 1050 | 1050 | 1050 | 1050 |
| Isobutane WHSV, $hr^{-1}$ | 2.9 | 3.0 | 2.9 | 3.0 | 2.9 | 2.9 | 2.9 | 2.9 | 2.9 | 2.9 |
| Time on Stream, hrs | 145.4 | 152.2 | 169.0 | 176 | 191.4 | 199.7 | 216.1 | 222.2 | 241.7 | 248.2 |
| Product Composition (mol %) | | | | | | | | | | |
| Hydrogen | 28.37 | 32.12 | 32.19 | 32.61 | 33.05 | 32.55 | 32.35 | 32.73 | 32.42 | 32.66 |
| Methane | 0.44 | 0.63 | 0.64 | 0.63 | 0.58 | 0.57 | 0.56 | 0.54 | 0.54 | 0.52 |
| Ethane | 0.05 | 0.10 | 0.12 | 0.13 | 0.11 | 0.11 | 0.18 | 0.11 | 0.11 | 0.11 |
| Ethylene | 0.00 | 0.00 | 0.01 | 0.01 | 0.01 | 0.01 | 0.01 | 0.00 | 0.01 | 0.01 |
| Propane | 0.36 | 0.46 | 0.43 | 0.46 | 0.41 | 0.41 | 0.38 | 0.41 | 0.38 | 0.40 |
| Propylene | 0.14 | 0.19 | 0.19 | 0.30 | 0.18 | 0.19 | 0.20 | 0.20 | 0.17 | 0.20 |
| Butane | 0.79 | 0.89 | 1.05 | 1.13 | 0.96 | 0.99 | 0.97 | 0.95 | 0.94 | 0.91 |
| Isobutane | 42.06 | 34.02 | 33.22 | 32.61 | 32.71 | 33.02 | 33.28 | 33.13 | 33.82 | 33.78 |
| 2-Butenes | 0.45 | 0.74 | 0.85 | 0.91 | 0.81 | 0.82 | 0.82 | 0.82 | 0.82 | 0.81 |
| 1,3-Butadiene | 0.00 | 0.06 | 0.07 | 0.10 | 0.07 | 0.07 | 0.07 | 0.07 | 0.07 | 0.07 |
| Isobutylene | 27.34 | 30.79 | 31.23 | 31.11 | 31.11 | 31.26 | 31.18 | 31.04 | 30.72 | 30.53 |
| C5+ | 0.00 | 0.00 | 0.00 | 0.00 | 0.00 | 0.00 | 0.00 | 0.00 | 0.00 | 0.00 |
| Results | | | | | | | | | | |
| Isobutane Conv. (%) | 41.28 | 49.88 | 51.01 | 51.61 | 51.14 | 51.04 | 50.81 | 50.75 | 49.96 | 49.84 |

TABLE 2-continued

| | | | | | | | | | | | |
|---|---|---|---|---|---|---|---|---|---|---|---|
| Isobutylene Sel. (%) | 92.46 | 9093 | 9029 | 89.45 | 90.86 | 90.79 | 90.72 | 90.92 | 91.00 | 90.97 | |
| Isobutylene Yld. (%) | 38.17 | 45.36 | 46.05 | 46.16 | 46.47 | 46.34 | 46.09 | 46.14 | 45.46 | 45.34 | |

Process Conditions

| | | | | | | | | | | | |
|---|---|---|---|---|---|---|---|---|---|---|---|
| Temperature, ° F. | 1050 | 1050 | 1050 | 1076 | 1076 | 1077 | 1076 | 1077 | 1077 | 1077 | 1076 | 1076 |
| Isobutane WHSV, hr$^{-1}$ | 3.0 | 3.0 | 3.0 | 3.0 | 3.0 | 3.0 | 3.0 | 2.9 | 3.0 | 2.9 | 3.0 | 2.9 |
| Time on Stream, hrs | 266.6 | 289.6 | 311.8 | 319.3 | 336.0 | 343.7 | 359.7 | 367.9 | 384.1 | 391.7 | 406.3 | 414.5 |

Product Composition (mol %)

| | | | | | | | | | | | | |
|---|---|---|---|---|---|---|---|---|---|---|---|---|
| Hydrogen | 32.20 | 31.93 | 31.44 | 32.84 | 32.73 | 32.79 | 32.13 | 31.63 | 31.79 | 31.49 | 31.04 | 30.95 |
| Methane | 0.59 | 0.59 | 0.73 | 1.00 | 0.95 | 0.95 | 0.92 | 1.12 | 1.10 | 1.11 | 1.06 | 1.09 |
| Ethane | 0.14 | 0.12 | 0.12 | 0.20 | 0.20 | 0.21 | 0.21 | 0.22 | 0.22 | 0.22 | 0.22 | 0.23 |
| Ethylene | 0.01 | 0.01 | 0.01 | 0.01 | 0.02 | 0.02 | 0.02 | 0.02 | 0.02 | 0.02 | 0.02 | 0.02 |
| Propane | 0.42 | 0.37 | 0.40 | 0.55 | 0.52 | 0.51 | 0.51 | 0.51 | 0.52 | 0.53 | 0.52 | 0.54 |
| Propyene | 0.19 | 0.21 | 0.19 | 0.33 | 0.32 | 0.32 | 0.34 | 0.51 | 0.37 | 0.39 | 0.39 | 0.39 |
| Butane | 1.09 | 1.00 | 1.00 | 0.99 | 0.94 | 0.95 | 0.93 | 1.05 | 0.91 | 0.91 | 0.87 | 0.86 |
| Isobutane | 34.12 | 34.75 | 35.36 | 32.05 | 32.69 | 32.66 | 33.67 | 34.03 | 34.63 | 34.87 | 35.84 | 35.99 |
| 2-Butenes | 0.91 | 0.91 | 0.91 | 1.15 | 1.11 | 1.14 | 1.13 | 1.22 | 1.15 | 1.15 | 1.11 | 1.12 |
| 1,3-Butadiene | 0.07 | 0.08 | 0.08 | 0.13 | 0.13 | 0.13 | 0.13 | 0.16 | 0.14 | 0.14 | 0.14 | 0.15 |
| Isobutylene | 30.26 | 30.03 | 29.76 | 30.75 | 30.39 | 30.32 | 30.01 | 29.53 | 29.15 | 29.17 | 28.77 | 28.66 |
| C5+ | 0.00 | 0.00 | 0.00 | 0.00 | 0.00 | 0.00 | 0.00 | 0.00 | 0.00 | 0.00 | 0.00 | 0.00 |

Results

| | | | | | | | | | | | | |
|---|---|---|---|---|---|---|---|---|---|---|---|---|
| Isobutane Conv. (%) | 49.68 | 48.95 | 48.42 | 52.28 | 51.40 | 51.41 | 50.39 | 50.23 | 49.23 | 49.10 | 48.03 | 47.88 |
| Isobutylene Sel. (%) | 89.85 | 90.13 | 89.64 | 87.58 | 87.88 | 87.76 | 87.75 | 85.99 | 86.81 | 86.71 | 86.87 | 86.69 |
| Isobutylene Yld. (%) | 44.64 | 44.12 | 43.40 | 45.79 | 45.17 | 45.12 | 44.22 | 43.19 | 42.74 | 42.58 | 41.72 | 41.51 |

TABLE 3

Process Conditions

| | | | | | | | | | |
|---|---|---|---|---|---|---|---|---|---|
| Temperature, ° F. | 1000 | 1000 | 1000 | 1000 | 999 | 998 | 996 | 998 | 1005 |
| Isobutane WHSV, hr$^{-1}$ | 5.8 | 5.9 | 6.0 | 5.9 | 6.0 | 6.0 | 6.0 | 5.9 | 6.0 |
| Time on Stream, hrs | 2.17 | 10.25 | 21.97 | 34.13 | 42.75 | 50.08 | 66.83 | 74.33 | 90.75 |

Product Composition (mol %)

| | | | | | | | | | |
|---|---|---|---|---|---|---|---|---|---|
| Hydrogen | 30.06 | 30.50 | 32.21 | 30.27 | 30.49 | 30.85 | 29.24 | 32.09 | 28.53 |
| Methane | 0.69 | 1.07 | 0.82 | 0.88 | 0.79 | 0.72 | 0.69 | 0.78 | 0.59 |
| Ethane | 2.85 | 1.88 | 1.15 | 1.13 | 0.95 | 0.85 | 0.73 | 0.84 | 0.54 |
| Ethylene | 0.07 | 0.05 | 0.03 | 0.03 | 0.02 | 0.02 | 0.01 | 0.02 | 0.01 |
| Propane | 1.16 | 0.97 | 0.81 | 0.82 | 0.69 | 0.79 | 0.70 | 0.80 | 0.63 |
| Propylene | 0.34 | 0.29 | 0.26 | 0.25 | 0.21 | 0.26 | 0.19 | 0.25 | 0.18 |
| Butane | 6.50 | 5.75 | 4.80 | 5.21 | 4.87 | 4.60 | 4.70 | 4.71 | 4.18 |
| Isobutane | 29.62 | 30.26 | 31.03 | 32.16 | 32.33 | 32.85 | 36.19 | 32.52 | 38.82 |
| 2-Butenes | 3.57 | 3.21 | 2.69 | 2.80 | 2.68 | 2.48 | 2.15 | 2.41 | 1.84 |
| 1,3-Butadiene | 0.00 | 0.00 | 0.00 | 0.00 | 0.00 | 0.00 | 0.00 | 0.00 | 0.00 |
| Isobutylene + 1-Butene | 25.12 | 26.01 | 26.20 | 26.45 | 26.97 | 26.58 | 24.40 | 25.58 | 24.68 |
| C5+ | 0.02 | 0.01 | 0.00 | 0.00 | 0.00 | 0.00 | 0.00 | 0.00 | 0.00 |

Results

| | | | | | | | | | |
|---|---|---|---|---|---|---|---|---|---|
| Isobutane Conv. (%) | 57.65 | 56.46 | 54.23 | 53.88 | 53.49 | 52.49 | 48.86 | 52.11 | 45.68 |
| Isobutylene Sel. (%) | 62.30 | 66.28 | 71.27 | 70.40 | 72.54 | 73.22 | 73.47 | 72.28 | 75.59 |
| Isobutylene Yld. (%) | 35.92 | 37.42 | 38.65 | 37.93 | 38.80 | 38.44 | 35.90 | 37.67 | 34.53 |

TABLE 4

Process Conditions

| | | | | | |
|---|---|---|---|---|---|
| Temperature, ° F. | 997 | 995 | 1002 | 1010 | 1014 |
| Isobutane WHSV, hr$^{-1}$ | 2.8 | 2.9 | 2.9 | 2.9 | 2.9 |
| Time on Stream, hrs | 3.1 | 5.7 | 6.6 | 21.9 | 28.2 |

Product Composition (mol %)

| | | | | | |
|---|---|---|---|---|---|
| Hydrogen | 22.04 | 20.64 | 20.84 | 6.78 | 3.73 |
| Methane | 3.24 | 1.84 | 1.76 | 0.26 | 0.14 |
| Ethane | 1.14 | 0.64 | 0.63 | 0.06 | 0.02 |
| Ethylene | 0.07 | 0.05 | 0.22 | 0.03 | 0.02 |
| Propane | 1.46 | 0.89 | 0.74 | 0.28 | 6.26 |
| Propylene | 0.90 | 0.63 | 0.62 | 0.28 | 0.24 |
| Butane | 1.36 | 0.85 | 0.70 | 0.16 | 0.16 |
| Isobutane | 46.02 | 52.77 | 53.42 | 84.42 | 90.27 |
| 2-Butenes | 1.44 | 1.09 | 1.05 | 0.14 | 0.06 |
| 1,3-Butadiene | 0.13 | 0.10 | 0.12 | 0.05 | 0.04 |
| Isobutylene + 1-Butene | 22.18 | 20.49 | 19.90 | 7.54 | 5.06 |
| C5+ | 0.02 | 0.01 | 0.01 | 0.00 | 0.00 |

Results

| | | | | | |
|---|---|---|---|---|---|
| Isobutane Conv. (%) | 41.00 | 33.51 | 32.52 | 9.44 | 6.23 |
| Isobutylene Sel. (%) | 69.44 | 77.06 | 77.31 | 85.68 | 84.32 |
| Isobutylene Yld. (%) | 28.47 | 25.82 | 25.14 | 8.05 | 5.25 |

TABLE 5

| Process Conditions | | | | | | | |
|---|---|---|---|---|---|---|---|
| Temperature, °F. | 1000 | 1000 | 1000 | 1000 | 1000 | 1000 | 1000 |
| Isobutane WHSV, hr$^{-1}$ | 2.9 | 2.9 | 2.9 | 2.9 | 2.9 | 2.9 | 2.9 |
| Time on Stream, hrs | 4.1 | 6.5 | 23.2 | 30.8 | 47.4 | 53.4 | 71.0 |
| Product Composition (mol %) | | | | | | | |
| Hydrogen | 30.20 | 29.31 | 27.72 | 25.86 | 25.15 | 23.85 | 21.09 |
| Methane | 0.15 | 0.14 | 0.15 | 0.13 | 0.15 | 0.15 | 0.15 |
| Ethane | 0.01 | 0.01 | 0.01 | 0.01 | 0.01 | 0.37 | 0.29 |
| Ethylene | 0.00 | 0.01 | 0.01 | 0.01 | 0.01 | 0.02 | 0.01 |
| Propane | 0.23 | 0.24 | 0.16 | 0.20 | 0.17 | 0.27 | 0.21 |
| Propylene | 0.15 | 0.19 | 0.11 | 0.14 | 0.11 | 0.24 | 0.19 |
| Butane | 0.30 | 0.27 | 0.22 | 0.18 | 0.16 | 0.15 | 0.14 |
| Isobutane | 40.42 | 41.54 | 44.59 | 47.95 | 50.43 | 52.24 | 57.55 |
| 2-Butenes | 0.13 | 0.12 | 0.06 | 0.10 | 0.05 | 0.05 | 0.08 |
| 1,3-Butadiene | 0.01 | 0.00 | 0.00 | 0.00 | 0.00 | 0.00 | 0.00 |
| Isobutylene + 1-Butene | 28.40 | 28.17 | 26.97 | 25.42 | 23.76 | 22.68 | 20.29 |
| C5+ | 0.00 | 0.00 | 0.00 | 0.00 | 0.00 | 0.00 | 0.00 |
| Results | | | | | | | |
| Isobutane Conv. (%) | 42.09 | 41.24 | 38.31 | 35.32 | 32.62 | 31.41 | 27.07 |
| Isobutylene Sel. (%) | 96.67 | 96.62 | 97.41 | 97.07 | 97.30 | 94.83 | 94.97 |
| Isobutylene Yld. (%) | 40.68 | 39.85 | 37.32 | 34.29 | 31.74 | 29.78 | 25.71 |

TABLE 6

| Process Conditions | | | | | | |
|---|---|---|---|---|---|---|
| Temperature, °F. | 1000 | 1001 | 1001 | 1001 | 1001 | 1002 |
| Isobutane WHSV, hr$^{-1}$ | 2.9 | 2.9 | 2.9 | 2.9 | 2.9 | 2.9 |
| Time on Stream, hrs | 4.0 | 5.6 | 21.8 | 29.5 | 45.8 | 52.8 |
| Product Composition (mol %) | | | | | | |
| Hydrogen | 28.17 | 27.48 | 23.69 | 23.29 | 19.93 | 19.36 |
| Methane | 0.13 | 0.12 | 0.09 | 0.09 | 0.09 | 0.10 |
| Ethane | 0.01 | 0.01 | 0.00 | 0.00 | 0.00 | 0.00 |
| Ethylene | 0.01 | 0.00 | 0.00 | 0.00 | 0.00 | 0.00 |
| Propane | 0.24 | 0.22 | 0.24 | 0.25 | 0.18 | 0.19 |
| Propylene | 0.17 | 0.15 | 0.35 | 0.37 | 0.13 | 0.15 |
| Butane | 0.22 | 0.19 | 0.27 | 0.25 | 0.12 | 0.12 |
| Isobutane | 43.23 | 44.14 | 51.27 | 53.30 | 59.38 | 61.02 |
| 2-Butenes | 0.14 | 0.13 | 0.12 | 0.03 | 0.03 | 0.02 |
| 1,3-Butadiene | 0.00 | 0.00 | 0.00 | 0.00 | 0.00 | 0.00 |
| Isobutylene + 1-Butene | 27.68 | 27.56 | 23.97 | 22.44 | 20.14 | 19.04 |
| C5+ | 0.00 | 0.00 | 0.00 | 0.00 | 0.00 | 0.00 |
| Results | | | | | | |
| Isobutane Conv. (%) | 39.82 | 39.13 | 32.81 | 30.52 | 25.84 | 24.33 |
| Isobutylene Sel. (%) | 96.78 | 97.11 | 95.73 | 95.86 | 97.34 | 97.04 |
| Isobutylene Yld. (%) | 38.54 | 38.00 | 31.41 | 29.26 | 25.15 | 23.61 |

Catalyst 1, in accordance with the present invention and comprising platinum and zinc on a support comprising sodium, boroshicate, and silica, provided superior isobutane conversion, isobutylene selectivity, and isobutylene yields at a reaction temperature of about 1000° F. with isobutane conversion actually increasing slightly over time. After 150 hours, the reaction temperature was increased to about 1050° F. and isobutane conversion was increased substantially resulting in an isobutylene yield improvement of about 6 to 8 percent. There was only minor deactivation noticed. After 315 hours on stream, the reaction temperature was increased again to about 1075° F. and isobutane conversion was increased slightly just offsetting a slight loss in isobutylene selectivity. Overall, isobutane dehydrogenation with Catalyst 1 resulted in an isobutylene yield averaging in excess of 40 percent for an on-stream period of in excess of 400 hours. Over this 400 hour period, Catalyst 1 deactivated at a negligible percent conversion loss per day at a reaction temperature of 1000° F., a 0.6 percent conversion loss per day at a reaction temperature of 1050° F., and a 1.1 percent conversion loss per day at a reaction temperature of 1075° F.

Catalyst 2, a comparison catalyst comprising platinum and zinc on a support comprising borosilicate and silica and absent the sodium of Catalyst 1, provided higher isobutane conversion but substantially lower isobutylene selectivity than Catalyst 1, resulting in a substantially lower isobutylene yield of 37 percent. Moreover, Catalyst 2, without the sodium component, deactivated at a conversion loss per day of 3.1 percent at a reaction temperature of 1000° F., far exceeding the deactivation rate of the catalyst of the present invention.

Catalyst 3, a comparison catalyst comprising platinum on a support comprising sodium, borosilicate, and silica and absent the zinc of Catalyst 1, provided generally lower isobutane conversion and substantially lower isobutylene selectivity than Catalyst 1, resulting in a substantially lower isobutylene yield of 28 percent. Of equal importance, the maximum isobutylene yield was only maintained for a matter of hours. Overall, Catalyst 3, without the zinc component, deactivated at a conversion loss per day of 33.3 percent at a reaction temperature of 1000° F., far exceeding the deactivation rate of the catalyst of the present invention.

Catalyst 4, a comparison catalyst comprising platinum and zinc on a support comprising alumina and sodium and absent the borosilicate and silica of Catalyst 1, provided reasonable initial isobutane conversion, isobutylene selectivity, and isobutylene yield. The initial isobutane conversion and the initial isobutylene yield slightly exceeded 40 percent at a reaction temperature of 1000° F. However, within 71 hours, the isobutane conversion plummeted to less than 30 percent resulting in an isobutylene yield of less than 30 percent. Overall, Catalyst 4, substituting alumina for the support of the present invention, deactivated at a conversion loss per day of 5.4 percent, again far exceeding the deactivation rate of the catalyst of the present invention.

Catalyst 5, a comparison catalyst comprising platinum and tin (substituted for the zinc of Catalyst 1) on a support comprising alumina and absent the borosilicate and silica of Catalyst 1, provided reasonable initial isobutane conversion, isobutylene selectivity, and isobutylene yield. The initial isobutane conversion and the initial isobutylene yield were between 38 and 39 percent at a reaction temperature of 1000° F. However, within 30 hours, the isobutane conversion plummeted to less than 31 percent resulting in an isobutylene yield of less than 30 percent. Overall, Catalyst 5, substituting tin for the zinc of the present invention and further comprising alumina in place of the support of the present invention, deactivated at a conversion loss per day of 7.6 percent at a reaction temperature of 1000° F., again far exceeding the deactivation rate of the catalyst of the present invention.

TABLE 7

| Catalyst | Temperature, °F. | WHSV, hr$^{-1}$ | Deactivation, % Conversion/Day |
|---|---|---|---|
| Catalyst 1 | 1000 | 2.9 | N/A* |
| | 1050 | 2.9 | 0.6 |
| | 1075 | 2.9 | 1.1 |
| Catalyst 2 | 1000 | 6.0 | 3.2 |
| Catalyst 3 | 1000 | 2.9 | 33.3 |
| Catalyst 4 | 1000 | 2.9 | 5.4 |
| Catalyst 5 | 1000 | 2.9 | 7.6 |

*No apparent deactivation

EXAMPLE 7

A dehydrogenation catalyst in accordance with the present invention was regenerated for evaluation of catalyst performance after exposure of the catalyst to regeneration conditions. After dehydrogenating isobutane with Catalyst 1 for a period of 127 hours under the conditions set forth in Example 6, a portion of Catalyst 1 was regenerated ex-situ by placing it in an oven at 750° F. under a 0.5% oxygen/ 99.5% nitrogen atmosphere for a period of about 72 hours. The regenerated catalyst was designated as Catalyst 6. Isobutane was dehydrogenated over Catalyst 6 in a manner similar to that described in Example 6. The dehydrogenation results are set forth in Table 8.

EXAMPLE 8

Regenerated dehydrogenation Catalyst 6 was regenerated again after dehydrogenating isobutane for an additional on stream period of 158 hours. The catalyst was regenerated under the regeneration conditions of Example 7. The twice regenerated catalyst was designated as Catalyst 7. Isobutane was processed over Catalyst 7 in a manner similar to that described in Example 6. The dehydrogenation results are set forth in Table 8.

EXAMPLE 9

Twice regenerated dehydrogenation Catalyst 7 was regenerated again after dehydrogenating isobutane for an additional on stream period of 400 hours. The catalyst was regenerated under the regeneration conditions of Example 7. The thrice regenerated catalyst was designated as Catalyst 8. Isobutane was processed over Catalyst 8 in a manner similar to that described in Example 6. The dehydrogenation results are set forth in Table 8.

TABLE 8

| Process Conditions | | | | | | | | | |
|---|---|---|---|---|---|---|---|---|---|
| Temperature, ° F. | 1000 | 1000 | 1000 | 1000 | 1000 | 1000 | 1000 | 1002 | 1002 |
| Isobutane WHSV, $hr^{-1}$ | 2.7 | 2.9 | 2.9 | 2.9 | 3.0 | 2.9 | 2.9 | 3.2 | 3.2 |
| Time on Stream, hrs | 2.3 | 6.0 | 22.4 | 47.0 | 72.5 | 95.3 | 118.8 | 145.9 | 172.3 |
| Catalyst No. | 6 | 6 | 6 | 6 | 6 | 6 | 6 | 7 | 7 |
| Product Composition (mol %) | | | | | | | | | |
| Hydrogen | 27.53 | 26.89 | 27.59 | 26.76 | 27.04 | 27.85 | 27.52 | 30.55 | 30.52 |
| Methane | 0.21 | 0.19 | 0.16 | 0.16 | 0.14 | 0.09 | 0.18 | 0.10 | 0.11 |
| Ethane | 0.03 | 0.02 | 0.02 | 0.02 | 0.02 | 0.02 | 0.02 | 0.01 | 0.01 |
| Ethylene | 0.01 | 0.01 | 0.00 | 0.01 | 0.02 | 0.01 | 0.01 | 0.00 | 0.00 |
| Propane | 0.35 | 0.40 | 0.25 | 0.36 | 0.41 | 0.17 | 0.32 | 0.21 | 0.22 |
| Propylene | 0.18 | 0.42 | 0.11 | 0.38 | 0.52 | 0.13 | 0.29 | 0.13 | 0.14 |
| Butane | 0.51 | 0.69 | 0.46 | 0.74 | 0.65 | 0.68 | 0.81 | 0.37 | 0.42 |
| Isobutane | 44.47 | 44.54 | 44.56 | 44.58 | 45.02 | 44.29 | 43.93 | 39.02 | 38.93 |
| 2-Butenes | 0.25 | 0.50 | 0.21 | 0.48 | 0.27 | 0.30 | 0.41 | 0.21 | 0.23 |
| 1,3-Butadiene | 0.00 | 0.00 | 0.00 | 0.00 | 0.00 | 0.00 | 0.00 | 0.00 | 0.00 |
| Isobutylene + 1-Butene | 26.48 | 26.33 | 26.63 | 26.50 | 25.91 | 26.45 | 26.S0 | 29.40 | 29.41 |
| C5+ | 0.00 | 0.00 | 0.00 | 0.00 | 0.00 | 0.00 | 0.00 | 0.00 | 0.00 |
| Results | | | | | | | | | |
| Isobutane Conv. (%) | 38.65 | 39.08 | 38.46 | 39.14 | 38.29 | 38.61 | 39.39 | 43.81 | 43.96 |
| Isobutylene Sel. (%) | 94.52 | 92.14 | 95.63 | 92.45 | 92.75 | 94.95 | 92.82 | 96.63 | 96.29 |
| Isobutylene Yld. (%) | 36.53 | 36.01 | 36.78 | 36.19 | 35.51 | 36.66 | 36.56 | 42.33 | 42.33 |
| Process Conditions | | | | | | | | | |
| Temperature, ° F. | 1003 | 1005 | 1002 | 1005 | 998 | 1002 | 1002 | 1002 | 1003 |
| Isobutane WHSV, $hr^{-1}$ | 3.2 | 3.2 | 3.2 | 3.2 | 3.2 | 3.2 | 3.2 | 3.2 | 3.2 |
| Time on Stream, hrs | 193.9 | 213.7 | 237.3 | 261.2 | 284.9 | 352.5 | 376.4 | 400.2 | 426.3 |
| Catalyst No. | 7 | 7 | 7 | 7 | 7 | 8 | 8 | 8 | 8 |
| Product Composition (mol %) | | | | | | | | | |
| Hydrogen | 23.07 | 31.04 | 30.54 | 30.81 | 30.15 | 31.06 | 30.74 | 30.75 | 30.57 |
| Methane | 0.04 | 0.13 | 0.14 | 0.16 | 0.17 | 0.15 | 0.16 | 0.18 | 0.21 |
| Ethane | 0.00 | 0.01 | 0.01 | 0.02 | 0.02 | 0.02 | 0.02 | 0.02 | 0.03 |
| Ethylene | 0.00 | 0.00 | 0.00 | 0.00 | 0.00 | 0.00 | 0.00 | 0.00 | 0.00 |
| Propane | 0.32 | 0.22 | 0.23 | 0.25 | 0.26 | 0.24 | 0.25 | 0.25 | 0.27 |
| Propylene | 0.00 | 0.07 | 0.08 | 0.09 | 0.09 | 0.09 | 0.09 | 0.09 | 0.09 |
| Butane | 0.28 | 0.54 | 0.59 | 0.66 | 0.72 | 0.65 | 0.70 | 0.74 | 0.87 |
| Isobutane | 53.05 | 37.96 | 38.72 | 38.18 | 39.15 | 38.47 | 38.73 | 38.57 | 38.89 |
| 2-Butenes | 0.00 | 0.26 | 0.28 | 0.32 | 0.33 | 0.31 | 0.33 | 0.41 | 0.47 |
| 1,3-Butadiene | 0.00 | 0.01 | 0.01 | 0.01 | 0.01 | 0.01 | 0.01 | 0.00 | 0.00 |
| Isobutylene + 1-Butene | 23.25 | 29.75 | 29.41 | 29.51 | 29.11 | 29.01 | 28.97 | 29.00 | 28.60 |
| C5+ | 0.00 | 0.00 | 0.00 | 0.00 | 0.00 | 0.00 | 0.00 | 0.00 | 0.00 |
| Results | | | | | | | | | |
| Isobutane Conv. (%) | 31.04 | 44.95 | 44.26 | 44.82 | 43.95 | 44.19 | 44.07 | 44.31 | 43.98 |
| Isobutylene Sel. (%) | 97.36 | 95.99 | 95.66 | 95.14 | 94.83 | 95.21 | 94.91 | 94.52 | 93.68 |
| Isobutylene Yld. (%) | 30.22 | 43.15 | 42.34 | 42.65 | 41.68 | 42.07 | 41.83 | 41.88 | 41.19 |
| Process Conditions | | | | | | | | | |
| Temperature, ° F. | 1002 | 1002 | 1003 | 1002 | 1002 | 1002 | 1002 | 1001 | 1001 |
| Isobutane WHSV, $hr^{-1}$ | 3.2 | 3.2 | 3.2 | 3.2 | 3.2 | 3.2 | 3.2 | 3.2 | 3.2 |

TABLE 8-continued

| Time on Stream, hrs | 448.2 | 519.7 | 540.4 | 564.6 | 588.6 | 613.3 | 684.9 | 748.2 | 773.5 |
|---|---|---|---|---|---|---|---|---|---|
| Catalyst No. | 8 | 8 | 8 | 8 | 8 | 8 | 8 | 8 | 8 |
| Product Composition (mol %) | | | | | | | | | |
| Hydrogen | 30.79 | 30.48 | 30.40 | 30.14 | 30.40 | 30.32 | 29.89 | 30.18 | 30.58 |
| Methane | 0.21 | 0.25 | 0.28 | 0.31 | 0.30 | 0.32 | 0.38 | 0.22 | 0.23 |
| Ethane | 0.03 | 0.04 | 0.05 | 0.05 | 0.05 | 0.05 | 0.07 | 0.03 | 0.03 |
| Ethylene | 0.00 | 0.00 | 0.00 | 0.00 | 0.00 | 0.00 | 0.00 | 0.00 | 0.00 |
| Propane | 0.27 | 0.31 | 0.31 | 0.33 | 0.33 | 0.34 | 0.38 | 0.28 | 0.28 |
| Propylene | 0.09 | 0.10 | 0.10 | 0.11 | 0.11 | 0.10 | 0.12 | 0.10 | 0.10 |
| Butane | 0.83 | 1.00 | 1.09 | 1.17 | 1.15 | 1.18 | 1.31 | 0.89 | 0.90 |
| Isobutane | 38.68 | 38.49 | 38.41 | 38.84 | 38.32 | 38.48 | 39.01 | 39.50 | 39.07 |
| 2-Butenes | 0.46 | 0.55 | 0.61 | 0.65 | 0.64 | 0.66 | 0.72 | 0.52 | 0.53 |
| 1,3-Butadiene | 0.00 | 0.00 | 0.00 | 0.00 | 0.00 | 0.00 | 0.00 | 0.00 | 0.00 |
| Isobutylene + 1-Butene | 28.66 | 28.78 | 28.76 | 28.40 | 28.70 | 28.55 | 28.12 | 28.28 | 28.28 |
| C5+ | 0.00 | 0.00 | 0.00 | 0.00 | 0.00 | 0.00 | 0.00 | 0.00 | 0.00 |
| Results | | | | | | | | | |
| Isobutane Conv. (%) | 44.14 | 44.63 | 44.82 | 44.40 | 44.94 | 44.78 | 44.36 | 43.43 | 43.73 |
| Isobutylene Sel. (%) | 93.83 | 92.76 | 92.19 | 91.56 | 91.74 | 91.49 | 90.41 | 93.25 | 93.17 |
| Isobutylene Yld. (%) | 41.41 | 41.40 | 41.32 | 40.66 | 41.23 | 40.97 | 40.11 | 40.50 | 40.74 |
| Process Conditions | | | | | | | | | |
| Temperature, ° F. | 1002 | 1001 | 1001 | 1001 | 1001 | 1003 | 1003 | 1002 | 1001 | 1001 |

| Isobutane WHSV, hr$^{-1}$ | 3.2 | 3.2 | 3.2 | 3.2 | 3.2 | 3.2 | 3.2 | 3.2 | 3.2 | 3.2 |
|---|---|---|---|---|---|---|---|---|---|---|
| Time on Stream, hrs | 797.5 | 822.5 | 845.5 | 916.3 | 940.3 | 964.2 | 988.2 | 1013.5 | 1084.2 | 1109.1 |
| Catalyst No. | 8 | 8 | 8 | 8 | 8 | 8 | 8 | 8 | 8 | 8 |
| Product Composition (mol %) | | | | | | | | | | |
| Hydrogen | 30.04 | 30.00 | 30.06 | 29.87 | 29.50 | 29.63 | 39.39 | 39.70 | 29.39 | 29.89 |
| Methane | 0.23 | 0.26 | 0.26 | 0.29 | 0.29 | 0.29 | 0.34 | 0.33 | 0.35 | 0.36 |
| Ethane | 0.03 | 0.04 | 0.04 | 0.04 | 0.04 | 0.05 | 0.05 | 0.05 | 0.06 | 0.06 |
| Ethylene | 0.00 | 0.00 | 0.00 | 0.00 | 0.00 | 0.00 | 0.00 | 0.00 | 0.00 | 0.00 |
| Propane | 0.29 | 0.30 | 0.29 | 0.34 | 0.32 | 0.32 | 0.34 | 0.35 | 0.36 | 0.36 |
| Propylene | 0.10 | 0.10 | 0.10 | 0.11 | 0.11 | 0.11 | 0.12 | 0.12 | 0.13 | 0.13 |
| Butane | 0.90 | 0.94 | 0.92 | 0.93 | 0.92 | 0.92 | 1.00 | 0.99 | 0.98 | 0.97 |
| Isobutane | 39.68 | 39.43 | 39.83 | 40.18 | 40.62 | 40.44 | 40.64 | 40.10 | 40.70 | 41.26 |
| 2-Butenes | 0.46 | 0.56 | 0.54 | 0.52 | 0.55 | 0.57 | 0.61 | 0.58 | 0.62 | 0.62 |
| 1,3-Butadiene | 0.00 | 0.00 | 0.00 | 0.03 | 0.00 | 0.00 | 0.00 | 0.03 | 0.00 | 0.00 |
| Isobutylene + 1-Butene | 28.25 | 28.36 | 27.96 | 27.70 | 27.65 | 27.67 | 27.52 | 27.75 | 27.41 | 27.35 |
| C5+ | 0.00 | 0.00 | 0.00 | 0.00 | 0.00 | 0.00 | 0.00 | 0.00 | 0.00 | 0.00 |
| Results | | | | | | | | | | |
| Isobutane Conv. (%) | 43.27 | 43.66 | 43.05 | 42.71 | 42.38 | 42.52 | 42.45 | 42.96 | 42.37 | 41.98 |
| Isobutylene Sel. (%) | 93.34 | 92.78 | 92.88 | 92.46 | 92.52 | 92.47 | 91.82 | 91.88 | 91.63 | 91.63 |
| Isobutylene Yld. (%) | 40.39 | 40.51 | 39.98 | 39.49 | 39.21 | 39.32 | 38.97 | 39.47 | 38.82 | 38.46 |

Examples 7–9 and Catalysts 6–8 illustrate that the dehydrogenation catalyst in accordance with the present invention can catalyze dehydrogenation for a period of in excess of 1100 hours on stream while still maintaining superior yields of isobutylene. Additionally, Catalysts 6–8 illustrate that a catalyst in accordance with the present invention can undergo multiple regeneration sequences while maintaining superior performance. Over the 1100+ hour span of the test, isobutane conversion actually increased about 3.5 percent while isobutylene selectivity fell about 3.0 percent resulting in an isobutylene yield that actually increased about 2.0 percent from 36.5 percent to about 38.5 percent. Therefore, the catalyst in accordance with the present invention provides extraordinary stability advantages compared to the catalysts of the prior art that permit it to be regenerated over and over while still maintaining superior olefin yields.

EXAMPLE 10

A feedstock containing 99.5 weight percent propane was dehydrogenated over dehydrogenation Catalyst 1 of Example 1 in a manner similar to that described in Example 6.

The catalyst testing conditions, product composition, and performance criteria in terms of propane conversion, propylene selectivity, and propylene yield (defined hereabove) were determined for ascending time on stream. The results for use of Catalyst 1 with a propane feedstock are set forth in Table 9.

The use of Catalyst 1 for propane dehydrogenation provided lower paraffin (propane) conversion than for isobutane dehydrogenation at 26 percent, largely because of the less favorable thermodynamic equilibrium properties attendant to propane. However, olefin (propylene) selectivity was maintained at 97 percent. Moreover, propane conversion actually increased over time at a faster rate than propylene selectivity was reduced, resulting in an actual increased in propylene yield and dehydrogenation performance. The dehydrogenation catalyst of the present invention maintained this performance over an on stream run length of over 150 hours.

TABLE 9

| Process Conditions | | | | | | | | | | |
|---|---|---|---|---|---|---|---|---|---|---|
| Temperature, °F. | 1004 | 1004 | 1003.9 | 1003.9 | 1003.9 | 1004 | 1004 | 1003.9 | 1004 | 1003.9 |
| Propane WHSV, hr$^{-1}$ | 11.9 | 11.9 | 11.9 | 11.9 | 11.9 | 11.9 | 11.9 | 11.9 | 11.9 | 11.9 |
| Time on Stream, hrs | 1.4 | 4.0 | 6.2 | 8.4 | 11.0 | 16.3 | 26.1 | 36.0 | 45.3 | 55.1 |
| Product Composition (mol %) | | | | | | | | | | |
| Hydrogen | 17.80 | 17.70 | 17.80 | 17.70 | 17.85 | 17.60 | 17.75 | 18.30 | 19.00 | 19.27 |
| Methane | 0.00 | 0.00 | 0.00 | 0.00 | 0.00 | 0.00 | 0.00 | 0.00 | 0.00 | 0.00 |
| Ethane | 0.20 | 0.20 | 0.19 | 0.19 | 0.19 | 0.18 | 0.18 | 0.18 | 0.17 | 0.17 |
| Ethylene | 0.01 | 0.01 | 0.01 | 0.01 | 0.01 | 0.01 | 0.01 | 0.01 | 0.01 | 0.01 |
| Propane | 63.92 | 63.96 | 64.01 | 63.99 | 63.79 | 64.44 | 64.00 | 62.80 | 61.68 | 60.92 |
| Propylene | 17.87 | 17.85 | 17.83 | 17.84 | 17.94 | 17.62 | 17.84 | 18.43 | 19.0 | 19.39 |
| Butane | 0.00 | 0.00 | 0.00 | 0.00 | 0.00 | 0.00 | 0.00 | 0.00 | 0.00 | 0.00 |
| Isobutane | 0.10 | 0.10 | 0.10 | 0.10 | 0.10 | 0.10 | 0.10 | 0.10 | 0.09 | 0.09 |
| 2-Butenes | 0.00 | 0.00 | 0.00 | 0.00 | 0.00 | 0.00 | 0.00 | 0.00 | 0.00 | 0.00 |
| 1,3-Butadiene | 0.00 | 0.00 | 0.00 | 0.00 | 0.00 | 0.00 | 0.00 | 0.00 | 0.00 | 0.00 |
| Isobutylene | 0.02 | 0.02 | 0.02 | 0.02 | 0.02 | 0.02 | 0.02 | 0.03 | 0.03 | 0.03 |
| C5+ | 0.00 | 0.00 | 0.00 | 0.00 | 0.00 | 0.00 | 0.00 | 0.00 | 0.00 | 0.00 |
| Results | | | | | | | | | | |
| Propane Conv. (%) | 26.06 | 25.82 | 25.71 | 25.52 | 25.84 | 25.34 | 25.76 | 26.26 | 27.66 | 27.67 |
| Propylene Sel. (%) | 99.15 | 99.2 | 96.6 | 98.7 | 97.3 | 96.5 | 96.2 | 96.5 | 95.0 | 96.2 |
| Propylene Yld. (%) | 25.84 | 25.61 | 24.84 | 25.19 | 25.14 | 24.45 | 24.78 | 25.34 | 26.28 | 26.62 |
| Process Conditions | | | | | | | | | | |
| Temperature, °F. | 1004 | 1004 | 1004 | 1004 | 1004 | 1004 | 1004 | 1004 | 1004 | 1004 |
| Propane WHSV, hr$^{-1}$ | 11.9 | 11.9 | 11.9 | 11.9 | 11.9 | 11.9 | 11.9 | 11.9 | 11.9 | 11.9 |
| Time on Stream, hrs | 88.0 | 94.0 | 98.5 | 108.3 | 113.2 | 118.1 | 127.6 | 132.5 | 142.3 | 152.1 |
| Product Composition (mol %) | | | | | | | | | | |
| Hydrogen | 20.00 | 20.05 | 20.15 | 20.10 | 20.10 | 20.05 | 20.15 | 20.11 | 20.07 | 20.00 |
| Methane | 0.00 | 0.00 | 0.00 | 0.00 | 00.0 | 0.00 | 0.00 | 0.00 | 0.00 | 0.00 |
| Ethane | 0.16 | 0.16 | 0.16 | 0.15 | 0.15 | 0.15 | 0.14 | 0.14 | 0.14 | 0.13 |
| Ethylene | 0.01 | 0.01 | 0.01 | 0.01 | 0.01 | 0.01 | 0.01 | 0.01 | 0.01 | 0.01 |
| Propane | 59.42 | 59.36 | 59.25 | 59.32 | 59.24 | 59.44 | 59.36 | 59.45 | 59.34 | 59.60 |
| Propylene | 20.14 | 20.17 | 20.22 | 20.19 | 20.11 | 20.13 | 20.17 | 20.13 | 20.18 | 20.05 |
| Butane | 0.00 | 0.00 | 0.00 | 0.00 | 0.00 | 0.00 | 0.00 | 0.00 | 0.00 | 0.00 |
| Isobutane | 0.09 | 0.09 | 0.09 | 0.09 | 0.09 | 0.09 | 0.09 | 0.09 | 0.09 | 0.10 |
| 2-Butenes | 0.00 | 0.00 | 0.00 | 0.00 | 0.00 | 0.00 | 0.00 | 0.00 | 0.00 | 0.00 |
| 1,3-Butadiene | 0.00 | 0.00 | 0.00 | 0.00 | 0.00 | 0.00 | 0.00 | 0.00 | 0.00 | 0.00 |
| Isobutylene | 0.04 | 0.04 | 0.04 | 0.04 | 0.04 | 0.04 | 0.04 | 0.04 | 0.04 | 0.04 |
| C5+ | 0.00 | 0.00 | 0.00 | 0.00 | 0.00 | 0.00 | 0.00 | 0.00 | 0.00 | 0.00 |
| Results | | | | | | | | | | |
| Propane Conv. (%) | 27.75 | 28.00 | 27.97 | 27.97 | 28.64 | 28.76 | 29.04 | 28.14 | 29.14 | 29.14 |
| Propylene Sel. (%) | 99.50 | 99.50 | 99.50 | 97.30 | 94.70 | 93.00 | 93.10 | 99.20 | 94.50 | 93.50 |
| Propylene Yld. (%) | 27.61 | 27.86 | 27.83 | 27.12 | 27.12 | 26.04 | 27.04 | 27.91 | 27.54 | 27.25 |

Other embodiments of the invention will be apparent to those skilled in the art from a consideration of this specification or from practice of the invention disclosed herein. It is intended that this specification be considered as exemplary only with the true scope and spirit of the invention being indicated by the following claims.

That which is claimed is:

1. A process for dehydrogenating a hydrocarbon feedstock and producing an olefinic product, the process comprising:
    contacting a hydrocarbon feedstock at dehydrogenation conditions with a dehydrogenation catalyst to produce an olefinic product; the dehydrogenation catalyst comprising about 0.01 to about 5.0 percent of a platinum group metal, about 0.02 weight percent to about 10.0 weight percent of zinc, an alkali metal and a borosilicate molecular sieve; the molecular sieve having been prepared directly in the hydrogen form containing less than about 100 ppm sodium or converted to the hydrogen form containing less than about 100 ppm sodium, thereafter impregnated with the platinum group metal and impregnated with zinc, and subsequently impregnated with the alkali metal; and
    recovering the olefinic product.

2. The process of claim 1 in which the platinum group metal is platinum.

3. The process of claim 1 in which the platinum group metal is palladium.

4. The process of claim 1 in which the alkali metal is sodium.

5. The process of claim 1 in which the molecular sieve is AMS-1B.

6. The process of claim 1 where the catalyst additionally comprises silica.

7. The process of claim 1 in which the catalyst additionally comprises a Group IVB metal.

8. The process of claim 7 in which the Group IVB metal is zirconium.

9. A process for dehydrogenating a hydrocarbon feedstock and producing an olefinic product, the process comprising:
    contacting a hydrocarbon feedstock at dehydrogenation conditions with a dehydrogenation catalyst to produce an olefinic product; the dehydrogenation catalyst comprising about 0.01 to about 5.0 percent of a platinum group metal, about 0.02 weight percent to about 10.0 weight percent of zinc, about 0.1 to about 10.0 weight percent of an alkali metal and a borosilicate molecular sieve; the molecular sieve having been prepared directly in the hydrogen form containing less than about 100 ppm sodium or converted to the hydrogen form containing less than about 100 ppm sodium, thereafter impregnated with the platinum group metal and impregnated with zinc, and subsequently impregnated to place the dehydrogenation catalyst alkali metal content within the above stated range of about 0.1 to about 10.0 weight percent; and recovering the olefinic product.

10. A process for dehydrogenating a hydrocarbon feedstock and producing an olefinic product, the process comprising:

contacting a hydrocarbon feedstock at dehydrogenation conditions with a dehydrogenation catalyst to produce an olefinic product; the dehydrogenation catalyst comprising about 0.01 to about 5.0 percent of a platinum group metal, about 0.02 weight percent to about 10.0 weight percent of zinc, about 0.1 to about 10.0 weight percent of sodium and a borosilicate molecular sieve; the molecular sieve having been prepared directly in the hydrogen form containing less than about 100 ppm sodium or converted to the hydrogen form containing less than about 100 ppm sodium, thereafter impregnated with the platinum group metal and impregnated with zinc, and subsequently impregnated to place the dehydrogenation catalyst sodium content within the above stated range of about 0.1 to about 10.0 weight percent; and recovering the olefinic product.

* * * * *

UNITED STATES PATENT AND TRADEMARK OFFICE
CERTIFICATE OF CORRECTION

PATENT NO. : 6,103,103
DATED : August 15, 2000
INVENTOR(S) : Bruce D. Alexander, George A. Huff, Jr., Mark P. Kaminsky It is certified that error appears in the above-identified patent and that said Letters Patent is hereby corrected as shown below:

Column 16,
Line 51, "catalyst was prepared by, first" should read -- catalyst was prepared by first --

Column 17,
Line 7, "to 20, mesh (U.S. Sieve" should read -- to 20 mesh (U.S. Sieve --
Lines 11-12, "the CAB-O-SIL" should read -- the CAB-O-SIL --

Column 23,
Line 52, "sodium, boroshicate, and silica," should read -- sodium, borosilicate, and silica --

Table2, column 19-20,
"Product Composition (mol %)   should    -- Product Composition (mol %)
1,3 Butadiene . . . 0.01 . . ."    read      1,3 Butadiene . . . 0.00 . . . --

"Product Composition (mol %)   should    -- Product Composition (mol %)
C5=    0.00 . . ." should read    read     C5+    0.00 . . . --

Table 2, column 21-22,
"Isobutylene Sel. (%)    92.46    9093    9029    89.45 . . ." should read -- Isobutylene Sel. (%)    92.46    90.93    90.29    89.45 . . . --

"Product Composition (mol %) should    -- Product Composition (mol %)
Propyene . . ."                  read       Propylene . . . --

Table 2, column 21
Line 64,
"Product Composition (mol %) should    -- Product Composition (mol %)
Propane . . . 6.26"              read       Propane . . . 0.26 --

UNITED STATES PATENT AND TRADEMARK OFFICE
CERTIFICATE OF CORRECTION

PATENT NO. : 6,103,103
DATED : August 15, 2000
INVENTOR(S) : Bruce D. Alexander, George A. Huff, Jr., Mark P. Kaminsky It is certified that error appears in the above-identified patent and that said Letters Patent is hereby corrected as shown below:

Table 8, column 25-26,
"Product Composition (mol %)   should read   -- Product Composition (mol %)
Isobutylene + 1-Butene . . . 26.SO . . ."        Isobutylene + 1-Butene . . . 26.50 . . . --

Signed and Sealed this

Thirteenth Day of November, 2001

Attest:

NICHOLAS P. GODICI
Attesting Officer    Acting Director of the United States Patent and Trademark Office